United States Patent
Gaudry et al.

(10) Patent No.: US 10,029,127 B2
(45) Date of Patent: Jul. 24, 2018

(54) ANHYDROUS ANTISUN CREAM COMPRISING A NON-EMULSIFYING ELASTOMERIC ORGANOPOLYSILOXANE, A MATTING AGENT AND A NON-SILICONE ORGANIC OIL THICKENER

(75) Inventors: Anne-Laure Gaudry, La Ferte Gaucher (FR); Cecile Boschet, L'Hay-les-Rofes (FR)

(73) Assignee: L'OREAL, Paris (FR)

( * ) Notice: Subject to any disclaimer, the term of this patent is extended or adjusted under 35 U.S.C. 154(b) by 33 days.

(21) Appl. No.: 14/123,860

(22) PCT Filed: May 25, 2012

(86) PCT No.: PCT/EP2012/059874
§ 371 (c)(1),
(2), (4) Date: Feb. 20, 2014

(87) PCT Pub. No.: WO2012/168102
PCT Pub. Date: Dec. 13, 2012

(65) Prior Publication Data
US 2014/0178317 A1    Jun. 26, 2014

Related U.S. Application Data

(60) Provisional application No. 61/495,128, filed on Jun. 9, 2011.

(30) Foreign Application Priority Data

Jun. 9, 2011  (FR) ..................................... 11 55033

(51) Int. Cl.
| | | |
|---|---|---|
| *A61K 8/58* | (2006.01) | |
| *A61K 8/25* | (2006.01) | |
| *A61K 8/81* | (2006.01) | |
| *A61K 8/891* | (2006.01) | |
| *A61Q 17/04* | (2006.01) | |

(52) U.S. Cl.
CPC ................ *A61Q 17/04* (2013.01); *A61K 8/25* (2013.01); *A61K 8/585* (2013.01); *A61K 8/8152* (2013.01); *A61K 8/891* (2013.01); *A61K 2800/30* (2013.01); *A61K 2800/31* (2013.01)

(58) Field of Classification Search
None
See application file for complete search history.

(56) References Cited

U.S. PATENT DOCUMENTS

2009/0041691 A1* 2/2009 Candau .................... A61K 8/11
424/60
2011/0033512 A1* 2/2011 Breyfogle .............. A61K 8/891
424/401

* cited by examiner

*Primary Examiner* — John D Pak
*Assistant Examiner* — Daniel L Branson
(74) *Attorney, Agent, or Firm* — Polsinelli PC

(57) ABSTRACT

The present invention relates to an anhydrous composition in cream form, characterized in that it comprises, in a cosmetically acceptable support: (a) at least one oily phase; (b) at least one non-emulsifying elastomeric organopolysiloxane; (b) a photoprotective system capable of screening out UV radiation; (c) at least one matting agent; (d) at least one non-silicone organic thickener for the oily phase, chosen from: (1) crystalline polymers, preferably semi-crystalline polymers, (2) fatty acid esters of dextrin, (3) hydrophobic-modified polysaccharides, (4) crystalline olefin copolymers, (5) crystalline polycondensates, (6) polymers of lipophilic polyamide type, (7) lipophilic polyureas and polyurethanes, (8) block polymers, (9) cholesterol-based liquid-crystal agents and mixtures thereof; the said composition not comprising any humectant.

17 Claims, No Drawings

ANHYDROUS ANTISUN CREAM COMPRISING A NON-EMULSIFYING ELASTOMERIC ORGANOPOLYSILOXANE, A MATTING AGENT AND A NON-SILICONE ORGANIC OIL THICKENER

CROSS REFERENCE TO RELATED APPLICATIONS

This application is a National Phase filing under 35 U.S.C. § 371 of PCT/EP2012/059874 filed on May 25, 2012; and this application claims priority to Application No. 1155033 filed in France on Jun. 9, 2011; and claims the benefit of U.S. Provisional Application No. 61/495,128 filed on Jun. 9, 2011. The entire contents of each of these applications are hereby incorporated by reference.

The present invention relates to an anhydrous composition in cream form, characterized in that it comprises, in a cosmetically acceptable support:
(a) at least one oily phase;
(b) at least one elastomeric organopolysiloxane;
(b) a photoprotective system capable of screening out UV radiation;
(c) at least one matting agent;
(d) at least one non-silicone organic thickener for the oily phase, chosen from:
(1) crystalline polymers, preferably semi-crystalline polymers,
(2) fatty acid esters of dextrin,
(3) hydrophobic-modified polysaccharides,
(4) crystalline olefin copolymers,
(5) crystalline polycondensates,
(6) polymers of lipophilic polyamide type,
(7) lipophilic polyureas and polyurethanes,
(8) block polymers,
(9) cholesterol-based liquid-crystal agents and mixtures thereof; the said composition not comprising any humectant.

It is known that light radiation with wavelengths of between 280 nm and 400 nm permits tanning of the human epidermis and that light rays with wavelengths between 280 and 320 nm, known as UV-B rays, prevent the development of a natural tan; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss of elasticity of the skin and the appearance of wrinkles leading to premature ageing of the skin. They promote triggering of the erythemal reaction or amplify this reaction in certain individuals and may even be the cause of phototoxic or photoallergic reactions. It is thus desirable also to screen out UV-A radiation.

Many cosmetic compositions for photoprotecting the skin (against UV-A and/or UV-B) have been proposed to date. Formulations that are easy for the users to apply to the skin are most particularly sought. These screening cosmetic compositions must moreover satisfy the regulations in terms of protection factor and especially the European regulation on antisun products, in particular on the protection ratio between UVB and UVA and more particularly the SPF/PPD ratio, which must be less than 3.

The efficacy of antisun compositions for UV-B protection is generally expressed by the sun protection factor (SPF), which is expressed mathematically by the ratio of the dose of UV radiation necessary to reach the erythema-forming threshold with the UV-screening agent to the dose of UV radiation necessary to reach the erythema-forming threshold without UV-screening agent. This factor thus concerns so the protection efficacy, the biological spectrum of action of which is centred in the UVB range, and consequently takes into account the protection with respect to this UV-B radiation.

To characterize the protection with respect to UV-A, the PPD (persistent pigment darkening) method, which measures the skin colour observed 2 to 4 hours after exposure of the skin to UV-A, is particularly recommended and used. This method has been adopted since 1996 by the Japanese Cosmetic Industry Association (JCIA) as official test procedure for the UV-A labelling of products and is frequently used by test laboratories in Europe and the United States (Japan Cosmetic Industry Association Technical Bulletin. Measurement Standards for UVA protection efficacy. Issued Nov. 21, 1995 and effective as of Jan. 1, 1996).

The UVAPPD sun protection factor (UVAPPD PF) is expressed mathematically by the ratio of the UV-A radiation dose necessary to reach the pigmentation threshold with the UV-screening agent (MPPDp) to the UV-A radiation dose necessary to reach the pigmentation threshold without UV-screening agent (MPPDnp).

$$UVA_{PPD}PF = \frac{MPPD_p}{MPPD_{np}}$$

Antisun compositions are quite often in the form of an emulsion of oil-in-water type (i.e. a cosmetically acceptable support consisting of an aqueous dispersing continuous phase and of an oily dispersed discontinuous phase) or of the water-in-oil type (i.e. a cosmetically acceptable support consisting of an oily dispersing continuous phase and of an aqueous dispersed discontinuous phase) which contains, in various concentrations, one or more standard lipophilic and/or hydrophilic organic screening agents, which are capable of selectively absorbing harmful UV rays, these screening agents (and the amounts thereof) being selected as a function of the desired sun protection factor.

However, antisun emulsions with high SPF and UV-A protection factors, generally containing a large amount of organic screening agents, have a tendency to produce a glossy aspect on the skin during their application, which consumers do not find aesthetic. To reduce this undesirable glossy effect, matting fillers are used, such as kaolinite, talc, cellulose microbeads, plant fibres, synthetic fibres, in particular polyamide fibres, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof. However, the addition of these fillers does not make it possible to obtain a long-lasting matting effect after application. Furthermore, the presence of these fillers in large amounts leads to difficulty in spreading on the skin and especially to a pilling phenomenon.

Anhydrous formulations comprising organic UV-screening agents, matting fillers, humectants, a non-emulsifying elastomeric organopolysiloxane and a silicone emulsifying surfactant have already been proposed in patent application WO 02/03935, especially in Examples XI to XXVIII.

Now, after research conducted in the field of photoprotection mentioned above, the Applicant has discovered that these compositions necessarily comprising humectant such as polyols, in particular glycerol, require the presence of a silicone emulsifying surfactant, without which they destabilize and become heterogeneous, with the appearance of grains and lumps, which are unacceptable for cosmetic use, being seen. Silicone emulsifying surfactants may occasionally cause tolerance problems in the case of sensitive skin and of children. They may also pose problems of compatibility with the fatty phase.

Anhydrous formulations comprising organic UV-screening agents, matting fillers, humectants, a non-emulsifying elastomeric organopolysiloxane and an emulsifying elastomeric organopolysiloxane have also been proposed in patent application WO 2007/148 293. These compositions impose the presence of an emulsifying elastomeric organopolysiloxane to obtain satisfactory stability, which is reflected by a homogeneous composition that does not undergo any exudation of oil; this limits the formulation possibilities.

There is thus still a need for a wide range of anhydrous UV antisun compositions, which are easy to spread on the skin (which do not pill), making it possible simultaneously to obtain high antisun protection that is equilibrated in the UVA and UVB ranges, a long-lasting matting effect and good stability without it being necessary to use emulsifiers such as silicone emulsifiers or emulsifying elastomeric silicones and without the drawbacks mentioned previously.

Now, after extensive research conducted in the field of photoprotection mentioned above, the Applicant has discovered, surprisingly, that this objective can be achieved by using an anhydrous composition in cream form comprising, in a cosmetically acceptable medium:
(a) at least one oily phase;
(b) at least one non-emulsifying elastomeric organopolysiloxane;
(b) a photoprotective system capable of screening out UV radiation;
(c) at least one matting agent;
(d) at least one non-silicone thickener for the oily phase, chosen from:
(1) crystalline polymers, preferably chosen from semicrystalline polymers,
(2) fatty acid esters of dextrin,
(3) hydrophobic-modified polysaccharides,
(4) crystalline olefin copolymers,
(5) crystalline polycondensates,
(6) polymers of lipophilic polyamide type,
(7) lipophilic polyureas and polyurethanes,
(8) block polymers,
(9) cholesterol-based liquid-crystal agents,
(10) waxes and mixtures thereof; the said composition not comprising any humectant.

This discovery forms the basis of the present invention.

Thus, in accordance with a first subject of the present invention, a composition is so proposed.

According to the invention, the term "photoprotective system capable of screening out UV radiation" is generally intended to denote any compound or any combination of compounds which, via mechanisms that are known per se for the absorption and/or reflection and/or scattering of UV-A and/or UV-B radiation, can prevent, or at least limit, the contact of the said radiation with a surface (skin, hair) onto which this or these compounds have been applied. In other words, these compounds may be UV-absorbing photoprotective organic screening agents or UV-scattering and/or UV-reflecting mineral pigments, and also mixtures thereof.

The term "anhydrous composition" means a composition containing less than 1% by weight of water, or even less than 0.5% water, and especially free of water, the water not being added during the preparation of the composition but corresponding to the residual water provided by the mixed ingredients.

The term "oily phase" means any organic phase that is liquid at room temperature, comprising at least one fatty substance in oil form and optionally other lipophilic or liposoluble substances such as cosmetic active agents or organic screening agents.

The term "composition in cream form" means any composition whose penetrometry can be measured and whose stiffness is greater than 20 g, especially ranging from 25 to 150 g, more preferentially from 40 to 80 g and even more preferentially from 50 to 70 g. The stiffness is measured at 25° C. using a TA XT2i texture analyser manufactured by the company Thermo, equipped with an SMS P/0-5 HS 0.5 inch diameter Hemispherical Delrin cylinder probe. The stiffness (expressed in grams) of each product is measured in compression by the said cylinder at a speed of 2 mm/s over a distance of 25 mm.

The term "cosmetically acceptable" means compatible with the skin and/or its integuments, which has a pleasant colour, odour and feel, and which does not cause any unacceptable discomfort (stinging, tautness or redness) liable to put the consumer off using this composition.

The term "humectant" means any polyhydroxylated alcohol (comprising at least two hydroxyl groups OH) that is capable of humidifying the skin, of reducing its scaling and of stimulating the removal of flakes that form on the skin. They are generally chosen from glycerol, sorbitol, hydroxypropylsorbitol, hexylene glycol, 1,3-butylene glycol, 1,2,6-hexanetriol, oxyethylenated or oxypropylenated glycerol, polyalkene glycols such as dipropylene glycol, and alkylene polyols such as polyethylene glycol and propylene glycol, or mixtures thereof.

The term "not containing any humectant" means containing less than 1% by weight of humectant, preferentially less than 0.5% by weight and better still less than 0.1% by weight relative to the total weight of the composition, or even being free of humectant.

The term "matting agent" means any substance or any material intended to make the skin visibly more matt and less shiny.

The term "oily-phase organic thickener" means a compound in simple molecular or polymeric form that is capable of increasing the viscosity of the fatty phase of the composition; the said compound not comprising any silane or organosiloxane groups in its structure; the said compound comprising at least one carbon atom and at least one hydrogen atom in its structure.

The matting effect of the agent and/or composition containing it may especially be evaluated using a gonioreflectometer, by measuring the ratio R between the specular reflection and the scattered reflection. A value of R of less than or equal to 2 generally indicates a matting effect.

The term "composition with a long-lasting matting effect" means any formulation that shows a statistically significant reduction in the level of sheen measured at several experiment times from T10 min up to T6 hours relative to T0.

The measurement may be taken especially using a Samba® device, which is composed of a CCD camera and acquisition software. The volunteer is installed on a repositionable table enabling reproducibility of the measurements before and after application of the product. An image of the whole face is acquired using the software, and the analysis is then performed on each half-face. One half-face determined by randomization, receives 300 mg of product, and the other receives nothing. The measurements are taken on the two half-faces at T0, T10 minutes, T4 hours and T6 hours after application of the product.

Other characteristics, aspects and advantages of the present invention will emerge on reading the detailed description that follows.

Non-Emulsifying Elastomeric Organopolysiloxane

The term "non-emulsifying organopolysiloxane" means organopolysiloxane elastomers that do not contain a hydrophilic chain, such as polyoxyalkylene or polyglycerol units.

The crosslinked elastomeric organopolysiloxane in accordance with the invention may be obtained via a crosslinking addition reaction of diorganopolysiloxane containing at least one hydrogen bonded to silicon and of diorganopolysiloxane containing ethylenically unsaturated groups bonded to silicon, especially in the presence of a platinum catalyst; or via a dehydrogenation crosslinking condensation reaction between a diorganopolysiloxane containing hydroxyl end groups and a diorganopolysiloxane containing at least one hydrogen bonded to silicon, especially in the presence of an organotin; or via a crosslinking condensation reaction of a diorganopolysiloxane containing hydroxyl end groups and of a hydrolysable organopolysilane; or via thermal crosslinking of organopolysiloxane, especially in the presence of an organoperoxide catalyst; or via crosslinking of organopolysiloxane by high-energy radiation such as gamma rays, ultraviolet rays or an electron beam.

Preferably, the crosslinked organopolysiloxane elastomer is obtained by crosslinking addition reaction ($A_2$) of diorganopolysiloxane containing at least two so hydrogens each bonded to a silicon, and ($B_2$) of diorganopolysiloxane containing at least two ethylenically unsaturated groups bonded to silicon, especially in the presence ($C_2$) of a platinum catalyst, as described, for instance, in patent application EP-A-295 886.

In particular, the organopolysiloxane may be obtained by reaction of dimethylvinylsiloxy-terminated dimethylpolysiloxane and of trimethylsiloxy-terminated methylhydropolysiloxane, in the presence of a platinum catalyst.

Compound ($A_2$) is the base reagent for the formation of elastomeric organopolysiloxane, and the crosslinking takes place via an addition reaction of compound ($A_2$) with compound ($B_2$) in the presence of the catalyst ($C_2$).

Compound ($A_2$) is advantageously a diorganopolysiloxane containing at least two lower (for example of C2-C4) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane ($A_2$) may have a branched chain, linear chain, cyclic or network structure, but the linear chain structure is preferred. Compound ($A_2$) may have a viscosity ranging from the liquid state to the gum state. Preferably, compound ($A_2$) has a viscosity of at least 100 centistokes at 25° C.

The organopolysiloxanes ($A_2$) may be chosen from methylvinylsiloxanes, methylvinylsiloxane/dimethylsiloxane copolymers, dimethylvinylsiloxy-terminated dimethylpolysiloxanes, dimethylvinylsiloxy-terminated dimethylsiloxane/methylphenylsiloxane copolymers, dimethylvinylsiloxy-terminated dimethylsiloxane/diphenylsiloxane/ methylvinylsiloxane copolymers, trimethylsiloxy-terminated dimethylsiloxane/methylvinylsiloxane copolymers, trimethylsiloxy-terminated dimethylsiloxane/ methylphenylsiloxane/methylvinylsiloxane copolymers, dimethylvinylsiloxy-terminated methyl(3,3,3-trifluoropropyl)polysiloxanes, and dimethylvinylsiloxy-terminated dimethylsiloxane/methyl(3,3,3-trifluoropropyl)siloxane copolymers.

Compound ($B_2$) is in particular an organopolysiloxane containing at least two hydrogens bonded to silicon in each molecule and is thus the crosslinking agent for compound ($A_2$).

Advantageously, the sum of the number of ethylenic groups per molecule in compound ($A_2$) and the number of hydrogen atoms bonded to silicon per molecule in compound ($B_2$) is at least 4.

Compound ($B_2$) may be in any molecular structure, especially in a linear chain, branched chain or cyclic structure.

Compound ($B_2$) may have a viscosity at 25° C. ranging from 1 to 50 000 centistokes, especially so as to be miscible with compound (A).

It is advantageous for compound ($B_2$) to be added in an amount such that the molecular ratio between the total amount of hydrogen atoms bonded to silicon in compound ($B_2$) and the total amount of all the ethylenically unsaturated groups in compound ($A_2$) is in the range from 1/1 to 20/1.

Compound ($B_2$) may be chosen from trimethylsiloxy-terminated methylhydropolysiloxanes, trimethylsiloxy-terminated dimethylsiloxane/methylhydrosiloxane copolymers and dimethylsiloxane/methylhydrosiloxane cyclic copolymers.

Compound ($C_2$) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst ($C_2$) is preferably added in an amount of from 0.1 to 1000 parts by weight and better still from 1 to 100 parts by weight, as clean platinum metal, per 1000 parts by weight of the total amount of compounds ($A_2$) and ($B_2$).

Other organic groups may be bonded to silicon in the organopolysiloxanes (A2) and ($B_2$) described previously, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

According to one particular form of the invention, the non-emulsifying elastomeric organopolysiloxane used is in powder form.

As non-emulsifying elastomeric organopolysiloxanes, use may be made of those in powder form having the INCI name: Dimethicone/vinyl dimethicone crosspolymer, for instance the commercial products sold under the names Dow Corning 9505 Cosmetic Powder and Dow Corning 9506 Cosmetic Powder by the company Dow Corning.

According to one preferred embodiment, the non-emulsifying elastomeric organopolysiloxane is mixed with at least one volatile or non-volatile hydrocarbon-based oil and/or volatile or non-volatile silicone oil to form a gel. In these gels, the non-emulsifying elastomeric organopolysiloxane is in the form of non-spherical particles.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils, which are liquid at room temperature, having a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than $10^{-3}$ mmHg (0.13 Pa).

As other non-volatile hydrocarbon-based oils that may be used according to the invention, mention may be made especially of:

hydrocarbon-based oils of plant origin such as triglyceride esters, which are generally fatty acid triesters of glycerol, the fatty acids of which may have chain lengths varying from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, *macadamia* oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; or else caprylic/capric acid triglycerides, for instance those sold by the company Stéarineries Dubois or those sold under the names Miglyol 810, 812 and 818 by the company Dynamit Nobel, (ii) synthetic ethers containing from 10 to 40 carbon atoms;
(iii) linear or branched hydrocarbons of mineral or synthetic origin, such as petroleum jelly, polydecenes, hydrogenated polyisobutene such as Parleam, and squalane, and mixtures thereof;
(iv) synthetic esters, for instance the oils of formula RCOOR' in which R represents a linear or branched fatty acid residue comprising from 1 to 40 carbon atoms and R' represents a hydrocarbon-based chain that is especially branched, containing from 1 to 40 carbon atoms, on condition that R+R'≥10, for instance purcellin oil (cetostearyl octanoate), isopropyl myristate, isopropyl palmitate, $C_{12}$-$C_{15}$ alkyl benzoate, for instance the product sold under the trade name Finsolv TN or Witconol TN by the company Witco or Tegosoft TN by the company Evonik Goldschmidt, 2-ethyl phenyl benzoate, for instance the commercial product sold under the name X-Tend 226 by the company ISP, isopropyl lanolate, hexyl laurate, diisopropyl adipate, isononyl isononanoate, oleyl erucate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate, diisostearyl malate; and pentaerythritol esters; citrates or tartrates, for instance linear $C_{12}$-$C_{13}$ dialkyl tartrates, such as those sold under the name Cosmacol ETI by the company Enichem Augusta Industriale, and also linear $C_{14}$-$C_{15}$ dialkyl tartrates such as those sold under the name Cosmacol ETL by the same company; acetates;
(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;
(vi) higher fatty acids such as oleic acid, linoleic acid or linolenic acid;
(vii) carbonates such as dicaprylyl carbonate, for instance the product sold under the name Cetiol CC by the company Cognis;
(viii) fatty amides, for instance isopropyl N-lauroyl sarcosinate, for instance the product sold under the trade name Eldew SL205 from Ajinomoto; and mixtures thereof.

The volatile hydrocarbon-based oils may be chosen from hydrocarbon-based oils containing from 8 to 16 carbon atoms, and especially branched C8-C16 alkanes, for instance C8-C16 isoalkanes of petroleum origin (also known as isoparaffins), for instance isododecane (also known as 2,2,4,4,6-pentamethylheptane), isodecane and isohexadecane, and the alkanes described in the patent applications from the company Cognis WO 2007/068 371 or WO 2008/155 059 (mixtures of different alkanes differing by at least one carbon). These alkanes are obtained from fatty alcohols, which are themselves obtained from coconut oil or palm oil, the oils sold under the trade name Isopar or Permethyl, branched $C_8$-$C_{16}$ esters isohexyl neopentanoate, and mixtures thereof. Other volatile hydrocarbon-based oils, for instance petroleum distillates, especially those sold under the name Shell Solt by the company Shell, may also be used. According to one embodiment, the volatile solvent is chosen from volatile hydrocarbon-based oils containing from 8 to 16 carbon atoms, and mixtures thereof.

b) Silicone Oils

The non-volatile silicone oils may be chosen especially from non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Volatile silicone oils that may be mentioned, for example, include volatile linear or cyclic silicone oils, especially those with a viscosity 8 centistokes ($8×10^{-6} m^2/s$) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of linear volatile alkyltrisiloxane oils of general formula (I):

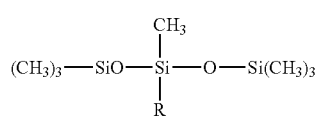

in which R represents an alkyl group containing from 2 to 4 carbon atoms, of which one or more hydrogen atoms may be substituted with a fluorine or chlorine atom.

Among the oils of general formula (I) that may be mentioned are:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As mixtures of oil/non-emulsifying elastomeric organopolysiloxane in gel form, use may be made of the products having the following INCI names:

Dimethicone and dimethicone/vinyl dimethicone crosspolymer, for instance the commercial products sold under the names KSG 6 and KSG 16 by the company Shin-Etsu, Cyclopentasiloxane and dimethicone/vinyl dimethicone crosspolymer, for instance the commercial products sold under the names KSG 15 and KSG 24 by the company Shin-Etsu; Dow Corning 9040 Silicone Elastomer Blend by the company Dow Corning;

Dimethicone and dimethicone crosspolymer, for instance the commercial product sold under the name Dow Corning 9041 Silicone Elastomer Blend by the company Dow Corning;

Mineral oil and vinyl dimethicone/lauryl dimethicone crosspolymer, for instance KSG 41 by the company Shin-Etsu;

Isododecane and vinyl dimethicone/lauryl dimethicone crosspolymer, for instance KSG 42 sold by the company Shin-Etsu;

Triethylhexanoin and vinyl dimethicone/lauryl dimethicone crosspolymer, for instance KSG 43 sold by the company Shin-Etsu;

Squalane and vinyl dimethicone/lauryl dimethicone crosspolymer, for instance KSG 44 sold by the company Shin-Etsu;

Use will be made more particularly of the non-emulsifying elastomeric organopolysiloxanes in gel form having the INCI name:—Dimethicone and dimethicone crosspolymer, for instance the commercial product sold under the name Dow Corning 9041 Silicone Elastomer Blend by the company Dow Corning.

The non-emulsifying elastomeric organopolysiloxane is preferably present in the composition in active material concentrations of greater than 1.5% by weight and especially ranging from 2% to 8% by weight and more preferentially ranging from 3% to 6% by weight relative to the total weight of the composition.

Non-Silicone Organic Oil-Phase Thickener

The non-silicone organic oil-phase thickener is preferably present in amounts ranging from 0.1% to 10%, more preferentially from 1% to 7% and even more preferentially from 4% to 7% relative to the total weight of the composition.

The non-silicone organic oil-phase thickener may be chosen from:
(1) crystalline polymers, preferably chosen from semicrystalline polymers,
(2) fatty acid esters of dextrin,
(3) hydrophobic-modified polysaccharides,
(4) crystalline olefin copolymers,
(5) crystalline polycondensates,
(6) polymers of lipophilic polyamide type,
(7) lipophilic polyureas and polyurethanes,
(8) block polymers,
(9) cholesterol-based liquid-crystal agents,
and mixtures thereof.

(1) Crystalline Polymers

Semicrystalline Polymers

The term "semicrystalline polymer" means polymers comprising a crystallizable portion, a crystallizable pendent and/or end chain or a crystallizable block in the backbone and/or at the ends, and an amorphous portion in the backbone, and having a first-order reversible temperature of change of phase, in particular of melting (solid-liquid transition). When the crystallizable portion is in the form of a crystallizable block of the polymer backbone, the amorphous portion of the polymer is in the form of an amorphous block; the semicrystalline polymer is, in this case, a block copolymer, for example of the diblock, triblock or multiblock type, comprising at least one crystallizable block and at least one amorphous block. The term "block" generally means at least five identical repeating units. The crystallizable block(s) are then of different chemical nature from the amorphous block(s).

The semicrystalline polymer according to the invention has a melting point of greater than or equal to 30° C. (especially ranging from 30° C. to 80° C.) and preferably ranging from 30° C. to 60° C. This melting point is a first-order temperature of change of state.

This melting point may be measured by any known method and in particular using a differential scanning calorimeter (DSC).

Advantageously, the semicrystalline polymer(s) to which the invention applies have a number-average molecular mass of greater than or equal to 1000.

Advantageously, the semicrystalline polymer(s) of the composition of the invention have a number-average molecular mass Mn ranging from 2000 to 800 000, preferably from 3000 to 500 000, better still from 4000 to 150 000 and especially less than 100 000 and better still from 4000 to 99 000. Preferably, they have a number-average molecular mass of greater than 5600, for example ranging from 5700 to 99 000.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer backbone. A "block" is a group of atoms belonging to the backbone, this group constituting one of the repeating units of the polymer. Advantageously, the "pendent crystallizable chain" may be a chain containing at least 6 carbon atoms.

Preferably, the crystallizable block(s) or chain(s) of the semicrystalline polymers represent at least 30% of the total weight of each polymer and better still at least 40%. The semicrystalline polymers of the invention containing crystallizable blocks are block or multiblock polymers. They may be obtained via polymerization of a monomer containing reactive double bonds (or ethylenic bonds) or via polycondensation. When the polymers of the invention are polymers containing crystallizable side chains, these side chains are advantageously in random or statistical form.

Preferably, the semicrystalline polymers that may be used in the composition according to the invention are of synthetic origin. Moreover, they do not comprise a polysaccharide backbone. In general, the crystallizable units (chains or blocks) of the semicrystalline polymers according to the invention originate from monomer(s) containing crystallizable block(s) or chain(s), used for the manufacture of the semicrystalline polymers.

According to the invention, the semicrystalline polymer may be chosen from block copolymers comprising at least one crystallizable block and at least one amorphous block, and homopolymers and copolymers bearing at least one crystallizable side chain per repeating unit, and mixtures thereof.

The semicrystalline polymers that may be used in the invention are in particular:

block copolymers of polyolefins with controlled crystallization, especially those whose monomers are described in EP-A-0 951 897, polycondensates, especially of aliphatic or aromatic polyester type or of aliphatic/aromatic copolyester type, homopolymers or copolymers bearing at least one crystallizable side chain and homopolymers or copolymers bearing at least one crystallizable block in the backbone, for instance those described in document U.S. Pat. No. 5,156,911, homopolymers or copolymers bearing at least one crystallizable side chain, in particular containing fluoro group(s), as described in document WO-A-01/19333, and mixtures thereof.

In the last two cases, the crystallizable side chain(s) or block(s) are hydrophobic.

a) Semicrystalline Polymers Containing Crystallizable Side Chains

Mention may be made in particular of those defined in documents U.S. Pat. No. 5,156,911 and WO-A-01/19333. They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned previously.

They can result:

from the polymerization, especially the free-radical polymerization, of one or more monomers containing reactive or ethylenic double bond(s) with respect to a polymerization, namely a vinyl, (meth)acrylic or allylic group, from the polycondensation of one or more monomers bearing co-reactive groups (carboxylic acid, sulfonic acid, alcohol, amine or isocyanate), such as, for example, polyesters, polyurethanes, polyethers, polyureas or polyamides.

In general, these polymers are chosen especially from homopolymers and copolymers resulting from the polymerization of at least one monomer containing crystallizable chain(s) that may be represented by formula (I):

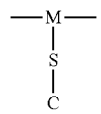

with M representing an atom of the polymer backbone, S representing a spacer and C representing a crystallizable group.

The crystallizable chains "—S—C" may be aliphatic or aromatic, and optionally fluorinated or perfluorinated. "S" especially represents a group $(CH_2)_n$ or $(CH_2CH_2O)_n$ or $(CH_2O)$, which may be linear or branched or cyclic, with n being an integer ranging from 0 to 22. Preferably, "S" is a linear group. Preferably, "S" and "C" are different.

When the crystallizable chains "—S—C" are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably $C_{14}$-$C_{24}$ alkyl chains. When they are fluoroalkyl or perfluoroalkyl chains, they contain at least six fluorinated carbon atoms and especially at least 11 carbon atoms, at least six of which carbon atoms are fluorinated.

As examples of semicrystalline polymers or copolymers bearing crystallizable chain(s), mention may be made of those resulting from the polymerization of one or more of the following monomers: (meth)acrylates of saturated alkyl with the alkyl group being $C_{14}$-$C_{24}$, perfluoroalkyl (meth)acrylates with a $C_{11}$-$C_{15}$ perfluoroalkyl group, N-alkyl (meth)acrylamides with the alkyl group being $C_{14}$ to $C_{24}$ with or without a fluorine atom, vinyl esters containing alkyl or perfluoro(alkyl) chains with the alkyl group being $C_{14}$ to $C_{24}$ (with at least 6 fluorine atoms per perfluoroalkyl chain), vinyl ethers containing alkyl or perfluoro(alkyl) chains with the alkyl group being $C_{14}$ to $C_{24}$ and at least 6 fluorine atoms per perfluoroalkyl chain, $C_{14}$ to $C_{24}$ alpha-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers that are the subject of the invention are copolymers, they additionally contain from 0 to 50% of groups Y or Z resulting from the copolymerization:

α) of Y which is a polar or non-polar monomer or a mixture of the two:

When Y is a polar monomer, it is either a monomer bearing polyoxyalkylenated groups (especially oxyethylenated and/or oxypropylenated groups), a hydroxyalkyl (meth)acrylate, for instance hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with a $C_1$ to $C_{10}$ alkyl group, for instance α-methylstyrene.

For the purposes of the invention, the term "alkyl" means a saturated group especially of $C_8$ to $C_{24}$, except where otherwise mentioned, and better still of $C_{14}$ to $C_{24}$.

β) of Z which is a polar monomer or a mixture of polar monomers. In this case, Z has the same definition as the "polar Y" defined above.

Preferably, the semicrystalline polymers containing a crystallizable side chain are alkyl (meth)acrylate or alkyl (meth)acrylamide homopolymers with an alkyl group as defined above, and especially of $C_{14}$-$C_{24}$, copolymers of these monomers with a hydrophilic monomer preferably of different nature from (meth)acrylic acid, for instance N-vinylpyrrolidone or hydroxyethyl (meth)acrylate, and mixtures thereof.

b) Polymers Bearing in the Backbone at Least One Crystallizable Block

These polymers are especially block copolymers consisting of at least two blocks of different chemical nature, one of which is crystallizable.

The block polymers defined in U.S. Pat. No. 5,156,911 may be used;

Block copolymers of olefin or of cycloolefin containing a crystallizable chain, for instance those derived from the block polymerization of:
cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-tetrahydronaphthalene, dicyclopenta-diene, or mixtures thereof,
with ethylene, propylene, 1-butene, 3-methyl-1-butene, 1-hexene, 4-methyl-1-pentene, 1-octene, 1-decene or 1-eicosene, or mixtures thereof.
and in particular copoly(ethylene/norbornene) blocks and (ethylene/propylene/ethylidene-norbornene) block terpolymers. Those resulting from the block copolymerization of at least two $C_2$-$C_{16}$, better still $C_2$-$C_{12}$ and even better still $C_4$-$C_{12}$ α-olefins such as those mentioned above and in particular block bipolymers of ethylene and of 1-octene may also be used.
The copolymers may be copolymers containing at least one crystallizable block, the copolymer residue being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:
Block that is crystallizable by nature: a) of polyester type, for instance poly(alkylene terephthalate), b) of polyolefin type, for instance polyethylenes or polypropylenes.
Amorphous and lipophilic block, for instance amorphous polyolefins or copoly(olefin)s such as poly(isobutylene), hydrogenated polybutadiene or hydrogenated poly(isoprene).
As examples of such copolymers containing a crystallizable block and a separate amorphous block, mention may be made of:
α) poly(ε-caprolactone)-b-poly(butadiene) block copolymers, preferably used hydrogenated, such as those described in the article "Melting behaviour of poly(ε-caprolactone)-block-polybutadiene copolymers" from S. Nojima, Macromolecules, 32, 3727-3734 (1999),
β) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995),
γ) the poly(ethylene)-b-copoly(ethylene/propylene) block copolymers cited in the articles "Morphology of semicrystalline block copolymers of ethylene-(ethylene-alt-propylene)" by P. Rangarajan et al., Macromolecules, 26, 4640-4645 (1993) and "Polymer aggregates with crystalline cores: the system poly(ethylene)poly(ethylene-propylene)" by P. Richter et al., Macromolecules, 30, 1053-1068 (1997).
δ) the poly(ethylene)-b-poly(ethylethylene) block copolymers mentioned in the general article "Crystallization in block copolymers" by I. W. Hamley, Advances in Polymer Science, vol. 148, 113-137 (1999).
The semicrystalline polymers in the composition of the invention may or may not be partially crosslinked, provided that the degree of crosslinking does not interfere with their dissolution or dispersion in the liquid fatty phase optionally present in the composition by heating above their melting point. It may then be a case of chemical crosslinking, by reaction with a multifunctional monomer during the polymerization. It may also be a case of physical crosslinking, which may then be due either to the establishment of bonds of hydrogen or dipolar type between groups borne by the polymer, for instance dipolar interactions between carboxylate ionomers, these interactions being in small amount and borne by the polymer backbone; or to a phase separation between the crystallizable blocks and the amorphous blocks, borne by the polymer.

Preferably, the semicrystalline polymers of the composition according to the invention are not crosslinked.

According to one particular embodiment of the invention, the polymer is chosen from copolymers resulting from the polymerization of at least one monomer containing a crystallizable chain chosen from saturated $C_{14}$ to $C_{24}$ alkyl (meth)acrylates, $C_{11}$ to $C_{15}$ perfluoroalkyl (meth)acrylates, $C_{14}$ to $C_{24}$ N-alkyl(meth)-acrylamides with or without a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ alpha-olefins, para-alkylstyrenes with an alkyl group containing from 12 to 24 carbon atoms, with at least one optionally fluorinated $C_1$ to $C_{10}$ monocarboxylic acid ester or amide, which may be represented by the following formula (ω):

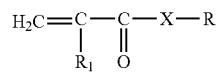

in which $R_1$ is H or $CH_3$, R represents an optionally fluorinated $C_1$-$C_{10}$ alkyl group and X represents O, NH or $NR_2$ in which $R_2$ represents an optionally fluorinated $C_1$-$C_{10}$ alkyl group.

According to one more particular embodiment of the invention, the polymer is derived from a monomer containing a crystallizable chain chosen from saturated $C_{14}$ to $C_{22}$ alkyl (meth)acrylates and even more particularly poly (stearyl acrylate) or poly(behenyl acrylate).

As particular examples of structuring semicrystalline polymers that may be used in the composition according to the invention, mention may be made of polymers having the INCI name "Poly C10-30 alkyl acrylate", for instance the Intelimer® products from the company Air Products, for instance the product Intelimer® IPA 13-1, which is a polystearyl acrylate, or the product Intelimer® IPA 13-6, which is a behenyl polymer.

The semicrystalline polymers may especially be:
those described in Examples 3, 4, 5, 7, 9 and 13 of U.S. Pat. No. 5,156,911 containing a —COOH group, resulting from the copolymerization of acrylic acid and of $C_5$ to $C_{16}$ alkyl (meth)acrylate and more particularly of the copolymerization:
of acrylic acid, of hexadecyl acrylate and of isodecyl acrylate in a 1/16/3 weight ratio,
of acrylic acid and of pentadecyl acrylate in a 1/19 weight ratio,
of acrylic acid, of hexadecyl acrylate and of ethyl acrylate in a 2.5/76.5/20 weight ratio,
of acrylic acid, of hexadecyl acrylate and of methyl acrylate in a 5/85/10 weight ratio,
of acrylic acid and of octadecyl methacrylate in a 2.5/97.5 weight ratio, of hexadecyl acrylate, of polyethylene glycol methacrylate monomethyl ether containing 8 ethylene glycol units, and of acrylic acid in an 8.5/1/0.5 weight ratio.

It is also possible to use the structure "0" from National Starch, as described in document U.S. Pat. No. 5,736,125, with a melting point of 44° C., and also semicrystalline polymers with crystallizable pendent chains comprising fluoro groups, as described in Examples 1, 4, 6, 7 and 8 of document WO-A-01/19333.

It is also possible to use the semicrystalline polymers obtained by copolymerization of stearyl acrylate and of acrylic acid or NVP as described in document U.S. Pat. No. 5,519,063 or EP-A-550 745, with melting points of 40° C. and 38° C., respectively.

It is also possible to use the semicrystalline polymers obtained by copolymerization of behenyl acrylate and of acrylic acid or NVP, as described in documents U.S. Pat. No. 5,519,063 and EP-A-550 745, with melting points of 60° C. and 58° C., respectively.

Preferably, the semicrystalline polymers do not comprise any carboxylic groups.

Finally, the semicrystalline polymers according to the invention may also be chosen from waxy polymers obtained by metallocene catalysis, such as those described in patent application US 2007/0 031 361.

These polymers are homopolymers or copolymers of ethylene and/or propylene prepared via metallocene catalysis, i.e. by polymerization at low pressure and in the presence of a metallocene catalyst.

The weight-average molecular mass (Mw) of the waxes obtained via metallocene catalysis described in that document is less than or equal to 25 000 g/mol and ranges, for example, from 2000 to 22 000 g/mol and better still from 4000 to 20 000 g/mol.

The number-average molecular mass (Mn) of the waxes obtained via metallocene catalysis described in that document is preferably less than or equal to 15 000 g/mol and ranges, for example, from 1000 to 12 000 g/mol and better still from 2000 to 10 000 g/mol.

The polydispersity index I of the polymer is equal to the ratio of the weight-average molecular mass Mw to the number-average molecular mass Mn. Preferably, the polydispersity index of the waxy polymers is between 1.5 and 10, preferably between 1.5 and 5, preferably between 1.5 and 3 and better still between 2 and 2.5.

The waxy homopolymers and copolymers may be obtained in a known manner from ethylene and/or propylene monomers, for example via metallocene catalysis according to the process described in document EP 571 882.

The homopolymers and copolymers of ethylene and/or propylene prepared via metallocene catalysis may be unmodified or "polar"-modified (polar-modified waxes, i.e. waxes modified such that they have the properties of a polar wax). The polar-modified waxy homopolymers and copolymers may be prepared in a known manner from unmodified waxy homopolymers and copolymers such as those described previously by oxidation with gases containing oxygen, such as air, or by grafting with polar monomers such as maleic acid or acrylic acid or alternatively derivatives of these acids. These two routes enabling polar modification of the polyolefins obtained via metallocene catalysis are described, respectively, in documents EP 890 583 and U.S. Pat. No. 5,998,547, for example, the content of these two documents being incorporated herein by reference.

According to the present invention, the polar-modified homopolymers and copolymers of ethylene and/or propylene prepared via metallocene catalysis that are particularly preferred are polymers modified such that they have hydrophilic properties. Examples that may be mentioned include ethylene and/or propylene homopolymers or copolymers modified by the presence of hydrophilic groups such as maleic anhydride, acrylate, methacrylate, polyvinylpyrrolidone (PVP), etc.

Waxy ethylene and/or propylene homopolymers or copolymers modified by the presence of hydrophilic groups such as maleic anhydride or acrylate are particularly preferred.

Examples that may be mentioned include:

polypropylene waxes modified with maleic anhydride (PPMA) sold by the company Clariant, or polypropylene-ethylene-maleic anhydride copolymers, such as those sold by the company Clariant under the name LicoCare, for instance LicoCare PP207 LP3349, LicoCare CM401 LP3345, LicoCare CA301 LP3346 and LicoCare CA302 LP3347 or alternatively the unmodified polyethylene waxes sold by the company Clariant, such as the product LicoCare PE 102 LP3329.

In the context of a composition for the lips, a polar-modified waxy polymer with a low degree of crystallinity, preferably of less than 40%, will be preferred.

(2) Fatty Acid Esters of Dextrin

The fatty acid esters of dextrin may be chosen especially from monoesters or polyesters of dextrin and of at least one fatty acid, and the compounds so corresponding to formula (III):

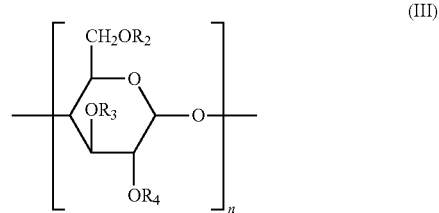

in which:

n is an integer ranging from 3 to 200, especially ranging from 20 to 150 and in particular ranging from 25 to 50, the radicals $R_2$, $R_3$ and $R_4$, which may be identical or different, are chosen from hydrogen and an acyl group (R—CO—) in which the radical R is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of the said radicals $R_2$, $R_3$ or $R_4$ is other than hydrogen.

In particular, $R_2$, $R_3$ and $R_4$ may represent hydrogen or an acyl group (R'—CO—) in which R' is a hydrocarbon-based radical as defined above, with the proviso that at least two of the said radicals $R_2$, $R_3$ or $R_4$ are identical and other than hydrogen.

The radicals $R_2$, $R_3$ and $R_4$ may all contain an acyl group (R'—CO), which is identical or different and especially identical.

In particular, n advantageously ranges from 25 to 50 and is especially equal to 38 in the general formula (III) of the ester according to the invention.

When the radicals $R_2$, $R_3$ and/or $R_4$, which may be identical or different, contain an acyl group (R'—CO), these radicals may be chosen especially from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, at least one dextrin palmitate is used as fatty acid ester of dextrin. This ester may be used alone or as a mixture with other esters.

Advantageously, the fatty acid ester of dextrin has a degree of substitution of less than or equal to 2.5, especially ranging from 1.5 to 2.5 and preferably from 2 to 2.5 on the basis of one glucose unit. The weight-average molecular weight of the dextrin ester may in particular be from 10 000 to 150 000, especially from 12 000 to 100 000 and even from 15 000 to 80 000.

Dextrin esters, in particular dextrin palmitates, are commercially available under the name Rheopearl TL or Rheopearl KL by the company Chiba Flour.

(3) Hydrophobic-modified Polysaccharides

The polysaccharide used in the present invention is preferably chosen from fructans.

Fructans or fructosans are oligosaccharides or polysaccharides comprising a sequence of anhydrofructose units optionally combined with several saccharide residues other than fructose. Fructans may be linear or branched. Fructans may be products obtained directly from a plant or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are for the most part linked via β-2-1 bonds. These are essentially linear fructans such as inulins. The second group also corresponds to linear fructoses, but the fructose units are essentially linked via β-2-6 bonds. These products are levans. The third group corresponds to mixed fructans, i.e. containing β-2-6 and β-2-1 sequences. These are essentially branched fructans, such as graminans.

The fructans used in the compositions according to the invention are inulins. Inulin may be obtained, for example, from chicory, dahlia or Jerusalem artichoke. Preferably, the inulin used in the composition according to the invention is obtained, for example, from chicory.

The polysaccharides, in particular the inulins, used in the compositions according to the invention are hydrophobic-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; divalent cycloaliphatic groups or organopolysiloxane chains. These hydrocarbon-based or organopolysiloxane chains may especially comprise one or more ester, amide, urethane, carbamate, thiocarbamate, urea, thiourea and/or sulfonamide functions especially such as methylenedicyclohexyl and isophorone; or divalent aromatic groups such as phenylene.

In particular, the polysaccharide, especially the inulin, has a degree of polymerization from 2 to about 1000 and preferably from 2 to about 60, and a degree of substitution of less than 2 on the basis of one fructose unit.

According to one preferred embodiment, the hydrophobic chains contain at least one alkyl carbamate group of formula R"—NH—CO— in which R" is an alkyl group containing from 1 to 22 carbon atoms.

According to one more preferred embodiment, the hydrophobic chains are lauryl carbamate groups.

In particular, as non-limiting illustrations of hydrophobic modified inulins that may be used in the compositions, mention may be made of stearoyl inulin, such as those sold under the names Lifidrem INST by the company Engelhard and Rheopearl INS by the company Ciba; palmitoyl inulin; undecylenoyl inulin, such as those sold under the names Lifidrem INUK and Lifidrem INUM by the company Engelhard; and inulin lauryl carbamate, such as the product sold under the name Inutec SP1 by the company Orafti.

In particular, the hydrophobic-modified polysaccharide is an inulin grafted with lauryl carbamate, which is obtained especially from the reaction of lauryl isocyanate with an inulin, in particular obtained from chicory. An example of these compounds that may especially be mentioned is the product sold under the name Inutec SP1 by the company Orafti.

(4) Crystalline Olefin Copolymers

The crystalline olefin copolymers used in the compositions of the present patent application may be any olefin copolymer, i.e. a copolymer comprising only olefin units, having a controlled and moderate crystalline nature, i.e. a degree of crystallinity of not more than 50%, preferably between 5% and 40% and better still between 10% and 35%.

These copolymers are generally elastomers or plastomers and may be synthesized via any known process, in particular via a radical route, via Ziegler-Natta catalysis or via metallocene catalysis, preferably via metallocene catalysis.

A first class of crystalline olefin copolymers that may be used in the compositions according to the invention is that of α-olefin copolymers, in particular of $C_2$-$C_{16}$ and better still $C_2$-$C_{12}$ α-olefin. Preferably, these copolymers are bipolymers or terpolymers and most particularly bipolymers.

Among the bipolymers that are recommended for the compositions of the invention, mention may be made of bipolymers of ethylene and of a $C_4$-$C_{16}$ and preferably $C_4$-$C_{12}$ α-olefin and bipolymers of propylene and of a $C_4$-$C_{16}$ and preferably $C_4$-$C_{12}$ α-olefin. More preferably, the α-olefin is chosen from 1-butene, 1-pentene, 1-hexene, 1-octene, 1-nonene, 1-decene, 1-undecene, 1-dodecene, 3,5, 5-trimethyl-1-hexene, 3-methyl-1-pentene and 4-methyl-1-pentene.

Among these monomers, 1-butene and 1-octene are particularly preferred. The content of α-olefin in the bipolymer is generally between 2 mol % and 40 mol %, preferably 3 mol % to 30 mol % and better still 4 mol % to 20 mol %.

The recommended ethylene-octene bipolymers are plastomers with an octene content of between 5.2 mol % and 6.2 mol % and a degree of crystallinity of between 28% and 38%, and elastomers with an octene content of between 8 so mol % and 14 mol % and a degree of crystallinity of between 10% and 28%.

These bipolymers are synthesized via metallocene catalysis.

Such bipolymers are sold by the company Dow Chemical under the trade names Affinity® (plastomers) and Engage® (elastomers).

Ethylene-butene bipolymers are sold by the company Exxon under the trade name Exact Resins®.

Among the terpolymers, mention may be made of terpolymers of ethylene, propylene and a $C_4$-$C_{16}$ and preferably $C_4$-$C_{12}$ α-olefin.

In these terpolymers, the contents of $C_4$-$C_{16}$ α-olefin are as indicated previously and the preferred α-olefins are butene, hexene and octene.

A second class of olefin copolymers that are suitable for use in the compositions according to the invention is that of copolymers of ethylene or of propylene and of a cycloolefin, in particular bipolymers.

Generally, the cycloolefin content of the copolymers is less than 20 mol %.

Among the cycloolefins that may be used, mention may be made of cyclobutene, cyclohexene, cyclooctadiene, norbornene, dimethanooctahydronaphthalene (DMON), ethylidenenorbornene, vinylnorbornene and 4-vinylcyclohexene.

The recommended copolymers of this class are copolymers of ethylene and of norbornene. The norbornene content of these copolymers is generally less than 18 mol % to have the required crystalline nature, and these copolymers are synthesized via metallocene catalysis.

Suitable ethylene/norbornene copolymers are sold by the companies Mitsui Petrochemical or Mitsui-Sekka under the trade name Apel® and by the company Hoechst-Celanese under the trade name Topas®.

Other recommended ethylene/cycloolefin copolymers are ethylene/cyclobutene and ethylene/cyclohexene bipolymers with a low content of cycloolefin, generally less than 20 mol %.

A third class of suitable olefin copolymers is formed by olefin copolymers of controlled tacticity, i.e. copolymers comprising units of different tacticity.

Among these copolymers of controlled tacticity, mention may be made of isotactic propylene/atactic propylene and syndiotactic propylene/atactic propylene copolymers.

The isotactic or syndiotactic units or blocks give the copolymer the crystalline nature, whereas the amorphous atactic units or blocks prevent excessive crystallinity of the copolymer and regulate the degree of crystallinity and also the morphology and size of the crystallites.

The content of isotactic or syndiotactic units, the units which give the copolymer the crystalline nature, is thus determined so as to obtain the desired percentage of crystallinity (≤50%) in the copolymer.

The content of tactic units is generally between 10 mol % and 80 mol %. However, preferably, the content of atactic units is less than 30 mol %.

These copolymers are synthesized via metallocene catalysis.

A fourth class of olefin copolymers that is suitable for use in the present invention is formed by copolymers of monoolefin and of diene, for example ethylene/butadiene, propylene/butadiene, ethylene/isoprene and propylene/isoprene bipolymers, and ethylene/propylene/diene terpolymers, also obtained via metallocene synthesis.

The proportion of diene units in the copolymer of controlled crystallization is generally between 3 mol % and 20 mol %.

To improve the control of the crystallinity of the copolymer, crystallization-impeding additives that promote the formation of small crystals may optionally be added to the composition according to the invention. These additives, although used in small proportion, constitute numerous small germination "sites" uniformly distributed in the bulk. These additives are typically crystals of an organic or mineral substance.

In the case of an organic additive that needs to crystallize, it should have a melting point higher than the melting region of the copolymer and should preferably form small crystals.

At a temperature above its melting point, this substance is preferably soluble in the mixture of the liquid fatty phase and of the polymer melt. Thus, during cooling, the initially-dissolved additive recrystallizes in the form of numerous small crystals widely dispersed in the mixture, and the polymer then recrystallizes to give small crystal domains due to the presence of the additive crystals. This polymer recrystallization technique is standard.

The degree of crystallization, size and morphology of the olefin copolymers according to the invention may also be adjusted by mixing a first olefin copolymer according to the invention with a second crystalline polymer or copolymer, which is partially compatible with the first olefin copolymer. The second polymer or copolymer may be an olefin copolymer according to the invention, but having a degree of crystallinity different from that of the first copolymer, including a degree of crystallinity higher than the degree of crystallinity of the olefin copolymers according to the invention.

The second crystallizable polymer may also be a polymer of different nature, for example a copolyethylene/vinyl acetate obtained by radical copolymerization or even a crystallizable polyethylene such as those usually used in cosmetics.

For further details regarding this method for adjusting the degree of crystallinity, reference may be made to the articles entitled "Elastomeric blends of homogeneous ethylene-octene copolymers", S. Bensason et al., Polymer, Volume 38, No. 15, 1997, pages 3913-19, and "Blends of homogeneous ethylene-octene copolymers", S. Bensason et al., Polymer, Volume 38, No. 14, 1997, pages 3513-20.

(5) Crystalline Polycondensates

The polycondensate that may be used may be obtained by reacting:

from 10% to 30% by weight, relative to the total weight of the polycondensate, of at least one polyol comprising 3 to 6 hydroxyl groups;

from 30% to 80% by weight, relative to the total weight of the polycondensate, of at least one saturated or unsaturated, linear, branched and/or cyclic non-aromatic monocarboxylic acid containing 6 to 32 carbon atoms;

from 0.1% to 10% by weight, relative to the total weight of the polycondensate, of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms;

from 5% to 40% by weight, relative to the total weight of the polycondensate, of at least one saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid.

Preferably, the polycondensate may be obtained by reacting:

10% by weight of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms; and from 15% to 30% by weight, relative to the total weight of the polycondensate, of at least one polyol comprising 3 to 6 hydroxyl groups; and from 30% to 40% by weight, relative to the total weight of the polycondensate, of at least one saturated or unsaturated, linear, branched and/or cyclic non-aromatic monocarboxylic acid comprising 6 to 32 carbon atoms; and from 10% to 25% by weight, relative to the total weight of the polycondensate, of at least one saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid;

these conditions being cumulative, then the ratio between the number of moles of aromatic monocarboxylic acid and the number of moles of non-aromatic monocarboxylic acid is between 0.08 and 0.70.

The polycondensate may also possibly be obtained by reacting:

from 10% to 30% by weight, relative to the total weight of the polycondensate, of at least one polyol comprising 3 to 6 hydroxyl groups;

from 45% to 80% by weight, relative to the total weight of the polycondensate, of at least one saturated, linear, branched and/or cyclic non-aromatic monocarboxylic acid containing 6 to 32 carbon atoms;

from 0.1% to 10% by weight, relative to the total weight of the polycondensate, of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms;

from 5% to 40% by weight, relative to the total weight of the polycondensate, of at least one saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid.

One of the constituents necessary for the preparation of the polycondensates according to the invention is a compound comprising 3 to 6 hydroxyl groups (polyol), especially 3 to 4 hydroxyl groups. A mixture of such polyols may obviously be used. The said polyol may especially be a linear, branched and/or cyclic, saturated or unsaturated carbon-based and especially hydrocarbon-based compound, containing 3 to 18 carbon atoms, especially 3 to 12 or even 4 to 10 carbon atoms, and 3 to 6 hydroxyl (OH) groups, and also possibly comprising one or more oxygen atoms intercalated in the chain (ether function). The said polyol is preferably a linear or branched saturated hydrocarbon-based compound containing 3 to 18 carbon atoms, especially 3 to 12 or even 4 to 10 carbon atoms, and 3 to 6 hydroxyl (OH) groups. It may be chosen, alone or as a mixture, from:

triols such as 1,2,4-butanetriol, 1,2,6-hexanetriol, trimethylolethane, trimethylolpropane or glycerol;

tetraols such as pentaerythritol (tetramethylolmethane), erythritol, diglycerol or ditrimethylolpropane;

pentols such as xylitol;

hexols such as sorbitol and mannitol; or alternatively dipentaerythritol or triglycerol.

Preferably, the polyol is chosen from glycerol, pentaerythritol, diglycerol and sorbitol, and mixtures thereof, and better still is pentaerythritol. The polyol, or the polyol mixture, preferably represents 10% to 30% by weight, especially 12% to 25% by weight and better still 14% to 22% by weight relative to the total weight of the final polycondensate.

Another constituent necessary for the preparation of the polycondensates according to the invention is a saturated or unsaturated, linear, branched and/or cyclic non-aromatic monocarboxylic acid comprising 6 to 32 carbon atoms, especially 8 to 28 carbon atoms and better still 10 to 24 or even 12 to 20 carbon atoms. A mixture of such non-aromatic monocarboxylic acids may obviously be used.

The term "non-aromatic monocarboxylic acid" means a compound of formula R'''COOH, in which R''' is a saturated or unsaturated, linear, branched and/or cyclic hydrocarbon-based radical containing 5 to 31 carbon atoms, especially 7 to 27 carbon atoms and better still 9 to 23 carbon atoms or even 11 to 19 carbon atoms.

Preferably, the radical R is saturated. Better still, the said radical R is linear or so branched, and preferentially of $C_5$-$C_{31}$ or even $C_{11}$-$C_{21}$.

In one particular embodiment of the invention, the non-aromatic monocarboxylic acid has a melting point of greater than or equal to 25° C., preferably greater than or equal to 28° C., or even 30° C.; the reason for this is that it has been found that, when such an acid is used, in particular in large amount, it is possible firstly to obtain good gloss and good staying power of the said gloss, and secondly to reduce the amount of waxes usually present in the intended composition.

Among the non-aromatic monocarboxylic acids that may be used, mention may be made, alone or as a mixture, of:

saturated monocarboxylic acids such as caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid;

unsaturated but non-aromatic monocarboxylic acids, such as caproleic acid, obtusilic acid, undecylenic acid, dodecylenic acid, linderic acid, myristoleic acid, physeteric acid, tsuzunic acid, palmitoleic acid, oleic acid, petroselinic acid, vaccenic acid, elaidic acid, gondoic acid, gadoleic acid, erucic acid, ketoleic acid, nervonic acid, linoleic acid, linolenic acid or arachidonic acid.

Among the non-aromatic monocarboxylic acids mentioned above with a melting point of greater than or equal to 25° C., mention may be made, alone or as a mixture, of:

among the saturated monocarboxylic acids: decanoic (capric) acid, lauric acid, tridecanoic acid, myristic acid, palmitic acid, stearic acid, arachidic acid, behenic acid, cerotic (hexacosanoic) acid;

among the unsaturated but non-aromatic monocarboxylic acids: petroselinic acid, vaccenic acid, elaidic acid, gondoic acid, gadoleic acid, erucic acid, nervonic acid.

2-Ethylhexanoic acid, isooctanoic acid, lauric acid, myristic acid, isoheptanoic acid, isononanoic acid, nonanoic acid, palmitic acid, isostearic acid, stearic acid or behenic acid, and mixtures thereof, and better still isostearic acid alone or stearic acid alone, may preferably be used.

The said non-aromatic monocarboxylic acid, or the mixture of the said acids, preferably represents 30% to 80% by weight, especially 40% to 75% by weight, or even 45% to 70% by weight and better still 50% to 65% by weight, relative to the total weight of the final polycondensate.

Another constituent necessary for the preparation of the polycondensates according to the invention is an aromatic monocarboxylic acid containing 7 to 11 carbon atoms, also optionally substituted with 1 to 3 saturated or unsaturated, linear, branched and/or cyclic alkyl radicals containing 1 to 32 carbon atoms, especially 2 to 12 or even 3 to 8 carbon atoms. A mixture of such aromatic monocarboxylic acids may obviously be used.

The term "aromatic monocarboxylic acid" means a compound of formula R""COOH in which R"" is an aromatic hydrocarbon-based radical comprising 6 to 10 carbon atoms, and in particular benzoic and naphthoic radicals. The said radical R"" may also be substituted with 1 to 3 saturated or unsaturated, linear, branched and/or cyclic alkyl radicals containing 1 to 32 carbon atoms, especially 2 to 12 or even 3 to 8 carbon atoms; and especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl and isooctyl. Among the aromatic monocarboxylic acids that may be used, mention may be made, alone or as a mixture, of benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid. Benzoic acid, 4-tert-butylbenzoic acid, o-toluic acid, m-toluic acid or 1-naphthoic acid, alone or as mixtures, and better still benzoic acid alone, may preferably be used. The said aromatic monocarboxylic acid, or the mixture of the said acids, preferably represents from 0.1% to 10% by weight, especially 0.5% to 9.95% by weight, better still from 1% to 9.5% by weight or even 1.5% to 8% by weight, relative to the total weight of the final polycondensate.

Another constituent necessary for the preparation of the polycondensates according to the invention is a saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid. A mixture of such polycarboxylic acids and/or anhydrides may obviously be used. The said polycarboxylic acid may especially be chosen from linear, branched and/or cyclic, saturated or unsaturated, or even aromatic, polycarboxylic acids containing 2 to 50 carbon atoms, especially 2 to 40 and in particular 3 to 36 carbon atoms, or even 3 to 18 and better still 4 to 12 carbon atoms, or even 4 to 10 carbon atoms; the said acid comprises at least two carboxylic groups COOH and preferably from 2 to 4 COOH groups.

Preferably, the said polycarboxylic acid is aliphatic and contains 2 to 36 carbon atoms, especially 3 to 18 carbon atoms or even 4 to 12 carbon atoms; or alternatively is aromatic and contains 8 to 12 carbon atoms. It preferably comprises 2 to 4 COOH groups. The cyclic anhydride of such a polycarboxylic acid may especially correspond to one of the following formulae:

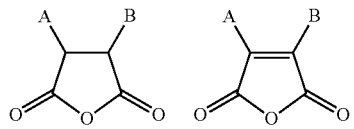

in which the groups A and B are, independently of each other:

a hydrogen atom;
a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl;
or alternatively A and B, taken together, form a saturated or unsaturated, or even aromatic, ring containing in total 5 to 7 and especially 6 carbon atoms.

Preferably, A and B represent a hydrogen atom or together form an aromatic ring containing in total 6 carbon atoms.

Among the polycarboxylic acids or anhydrides thereof that may be used, mention may be made, alone or as a mixture, of:

dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid, and fatty acid dimers (especially of $C_{36}$) such as the products sold under the names Pripol 1006, 1009, 1013 and 1017 by Uniqema;

tricarboxylic acids such as cyclohexanetricarboxylic acid, trimellitic acid, 1,2,3-benzenetricarboxylic acid or 1,3,5-benzenetricarboxylic acid;

tetracarboxylic acids such as butanetetracarboxylic acid and pyromellitic acid;

cyclic anhydrides of these acids and especially phthalic anhydride, trimellitic anhydride, maleic anhydride and succinic anhydride.

Adipic acid, phthalic anhydride and/or isophthalic acid, and better still isophthalic acid alone, may preferably be used.

The said polycarboxylic acid and/or the cyclic anhydride thereof preferably represents 5% to 40% by weight, especially 10% to 30% by weight and better still 14% to 25% by weight relative to the total weight of the final polycondensate.

The polycondensate according to the invention may also comprise a silicone containing hydroxyl (OH) and/or carboxylic (COOH) functions.

It may comprise 1 to 3 hydroxyl and/or carboxylic functions, and preferably comprises two hydroxyl functions or two carboxylic functions.

These functions may be located at the end of a chain or in the chain, but advantageously at the end of the chain.

In one preferred embodiment of the invention, the aromatic monocarboxylic acid is present in a molar amount greater than or equal to that of the non-aromatic monocarboxylic acid; in particular, the ratio between the number of moles of aromatic monocarboxylic acid and the number of moles of non-aromatic monocarboxylic acid is preferably between 0.08 and 0.70, especially between 0.10 and 0.60 and in particular between 0.12 and 0.40.

Preferably, the polycondensate according to the invention may be obtained by reacting:

at least one polyol chosen, alone or as a mixture, from 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or trig lycerol;

preferably present in an amount of 10% to 30% by weight, especially 12% to 25% by weight and better still 14% to 22% by weight, relative to the total weight of the final polycondensate;

at least one non-aromatic monocarboxylic acid chosen, alone or as a mixture, from caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid;

preferably present in an amount of 30% to 80% by weight, especially 40% to 75% by weight and better still 45% to 70% by weight relative to the total weight of the final polycondensate;

at least one aromatic monocarboxylic acid chosen, alone or as a mixture, from benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid;

preferably present in an amount of 0.1% to 10% by weight, especially 1% to 9.5% by weight and better still 1.5% to 8% by weight relative to the total weight of the final polycondensate; and at least one polycarboxylic acid or an anhydride thereof, chosen, alone or as a mixture, from decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride;

preferably present in an amount of 5% to 40% by weight, especially 10% to 30% by weight and better still 14% to 25% by weight relative to the total weight of the final polycondensate.

Preferentially, the polycondensate according to the invention may be obtained by reacting:

at least one polyol chosen, alone or as a mixture, from glycerol, pentaerythritol and sorbitol, and mixtures thereof, and better still pentaerythritol alone; present in an amount of 10% to 30% by weight, especially 12% to 25% by weight and better still 14% to 22% by weight relative to the total weight of the final polycondensate;

at least one non-aromatic monocarboxylic acid chosen, alone or as a mixture, from 2-ethylhexanoic acid, isooctanoic acid, lauric acid, palmitic acid, isostearic acid, isononanoic acid, stearic acid or behenic acid, and mixtures thereof, and better still isostearic acid alone or stearic acid alone;

present in an amount of 30% to 80% by weight, especially 40% to 75% by weight and better still 45% to 70% by weight relative to the total weight of the final polycondensate;

at least one aromatic monocarboxylic acid chosen, alone or as a mixture, from benzoic acid, o-toluic acid, m-toluic acid and 1-naphthoic acid, and better still benzoic acid alone; present in an amount of 0.1% to 10% by weight, especially 1% to 9.5% by weight, or even 1.5% to 8% by weight, relative to the total weight of the final polycondensate; and at least one polycarboxylic acid or an anhydride thereof, chosen, alone or as a mixture, from phthalic anhydride and isophthalic acid, and better still isophthalic acid alone; present in an amount of 5% to 40% by weight, especially 10% to 30% by weight and better still 14% to 25% by weight relative to the total weight of the final polycondensate.

The polycondensate according to the invention may be prepared via the esterification/polycondensation processes usually used by those skilled in the art.

By way of illustration, a general preparation process consists in:

mixing the polyol and the aromatic and non-aromatic monocarboxylic acids, heating the mixture under an inert atmosphere, first to the melting point (generally 100-130° C.) and then to a temperature of between 150 and 220° C. until the monocarboxylic acids have been totally consumed (achieved when the acid number is less than or equal to 1), preferably while gradually distilling off the water formed, then optionally cooling the mixture to a temperature of between 90 and 150° C., adding the polycarboxylic acid and/or the cyclic anhydride, and optionally the silicone containing hydroxyl or carboxylic functions, in a single portion or sequentially, and then heating again to a temperature of less than or equal to 220° C., especially between 170 and 220° C., preferably while continuing to remove the water formed, until the required characteristics in terms of acid number, viscosity, hydroxyl number and solubility are obtained.

It is possible to add conventional esterification catalysts, for example of sulfonic acid type (especially in a weight concentration of between 1% and 10%) or of titanate type (especially in a weight concentration of between 5 and 100 ppm).

It is also possible to perform the reaction, totally or partly, in an inert solvent such as xylene and/or under reduced pressure, to facilitate the removal of the water. Advantageously, neither catalyst nor solvent is used.

The said preparation process may also comprise a step of adding at least one antioxidant to the reaction medium, especially in a weight concentration of between 0.01% and 1% relative to the total weight of monomers, so as to limit the possible degradation associated with prolonged heating.

The antioxidant may be of primary type or secondary type, and may be chosen from hindered phenols, aromatic secondary amines, organophosphorus compounds, sulfur compounds, lactones and acrylic bisphenols; and mixtures thereof.

(6) Lipophilic Polyamide Polycondensates

For the purposes of the invention, the term "polycondensate" means a polymer obtained by polycondensation, i.e. by chemical reaction between monomers bearing different functional groups chosen in particular from acid, alcohol and amine functions.

For the purposes of the invention, the term "polymer" means a compound containing at least two repeating units, preferably at least three repeating units and better still ten repeating units.

The lipophilic polyamide polycondensate(s) are preferably present in the compositions of the invention in concentrations ranging from 0.1% to 15% by weight and more preferentially from 1% to 8% by weight relative to the total weight of the composition.

The lipophilic polyamide polycondensates may be chosen especially from polyamide polymers comprising a) a polymer backbone containing hydrocarbon-based repeating units bearing at least one non-pendent amide unit, and optionally b) at least one pendent fatty chain and/or at least one terminal fatty chain, which are optionally functionalized, comprising at least four carbon atoms and being bonded to these hydrocarbon-based units.

For the purposes of the invention, the term "functionalized chains" means an alkyl chain comprising one or more functional groups or reagents chosen especially from amide, hydroxyl, ether, oxyalkylene or polyoxyalkylene, halogen, including fluoro or perfluoro groups, and ester, siloxane and polysiloxane groups. In addition, the hydrogen atoms of one or more fatty chains may be at least partially replaced with fluorine atoms.

For the purposes of the invention, the term "hydrocarbon-based repeating units" means a unit comprising from 2 to 80 carbon atoms and preferably from 2 to 60 carbon atoms, bearing hydrogen atoms and optionally oxygen atoms, which may be linear, branched or cyclic, and saturated or unsaturated. These units each also comprise at least one amide group that is advantageously non-pendent, which is in the polymer backbone.

The pendent chains are advantageously bonded directly to at least one of the nitrogen atoms of the polymer backbone.

The lipophilic polyamide polycondensate may comprise between the hydrocarbon-based units silicone units or oxyalkylene units.

In addition, the lipophilic polyamide polycondensate of the composition of the invention advantageously comprises from 40% to 98% of fatty chains relative to the total number of amide units and fatty chains, and better still from 50% to 95%.

The pendent fatty chains are preferably bonded to at least one of the nitrogen atoms of the amide units of the polymer. In particular, the fatty chains of this polyamide represent from 40% to 98% of the total number of amide units and of fatty chains, and better still from 50% to 95%.

Advantageously, the lipophilic polyamide polycondensate has a weight-average molecular mass of less than 100 000 (especially ranging from 1000 to 100 000), in particular less than 50 000 (especially ranging from 1000 to 50 000) and more particularly ranging from 1000 to 30 000, preferably from 2000 to 20 000 and better still from 2000 to 10 000.

The lipophilic polyamide polycondensate is insoluble in water, especially at 25° C. In particular, it contains no ionic groups.

As preferred lipophilic polyamide polycondensates that may be used in the invention, mention may be made of polyamides branched with pendent fatty chains and/or terminal fatty chains containing from 6 to 120 carbon atoms and better still from 8 to 120 and in particular from 12 to 68 carbon atoms, each terminal fatty chain being bonded to the polyamide backbone via at least one bonding group L. The bonding group L may be chosen from ester, ether, amine, urea, urethane, thioester, thioether, thiourea and thiourethane groups. Preferably, these polymers comprise a fatty chain at each end of the polyamide backbone.

These polymers are preferably polymers resulting from a polycondensation between a dicarboxylic acid containing at least 32 carbon atoms (in particular containing from 32 to 44 carbon atoms) and an amine chosen from diamines containing at least 2 carbon atoms (in particular from 2 to 36 carbon atoms) and triamines containing at least 2 carbon atoms (in particular from 2 to 36 carbon atoms). The diacid is preferably a dimer of a fatty acid containing ethylenic unsaturation containing at least 16 carbon atoms, preferably from 16 to 24 carbon atoms, for instance oleic acid, linoleic acid or linolenic acid. The diamine is preferably ethylenediamine, hexylenediamine or hexamethylenediamine. The triamine is, for example, ethylenetriamine. For the polymers comprising one or two terminal carboxylic acid groups, it is advantageous to esterify them with a monoalcohol containing at least four carbon atoms, preferably from 10 to 36 carbon atoms, better still from 12 to 24 and even better from 16 to 24, for example 18 carbon atoms.

The lipophilic polyamide polycondensate of the composition according to the invention may be chosen in particular from the polymers of formula (V) below:

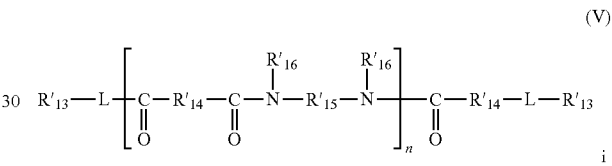

in which:

n is an integer ranging from 1 to 30;

$R'_{13}$ represents independently in each case a fatty chain and is chosen from an alkyl or alkenyl group containing at least 1 carbon atom and especially from 4 to 24 carbon atoms;

$R'_{14}$ represents independently in each case a hydrocarbon-based radical comprising from 1 to 52 carbon atoms;

$R'_{15}$ represents independently in each case an organic group comprising at least one atom chosen from carbon, hydrogen and nitrogen atoms, on condition that $R'_{15}$ comprises at least three carbon atoms;

$R'_{16}$ represents independently in each case: a hydrogen atom, an alkyl group comprising from 1 to 10 carbon atoms, or a direct bond to at least one group chosen from $R'_{15}$ and another $R'_{16}$ such that when the said group is another $R'_{16}$, the nitrogen atom to which are attached both $R'_{15}$ and $R'_{16}$ forms part of a heterocyclic structure defined by $R'_{16}$—N—$R'_{15}$, on condition that at least 50% of the $R'_4$ represent a hydrogen atom, and L represents a bonding group preferably chosen from ester, ether, amine, urea, urethane, thioester, thioether, thiourea and thiourethane, optionally substituted with at least one group $R'_1$ as defined above.

According to one embodiment, these polymers are chosen from the polymers of formula (V) in which the bonding group L represents an ester group

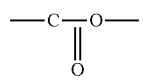

These polymers are more especially those described in document U.S. Pat. No. 5,783,657 from the company Union Camp.

Each of these polymers in particular satisfies formula (B) below:

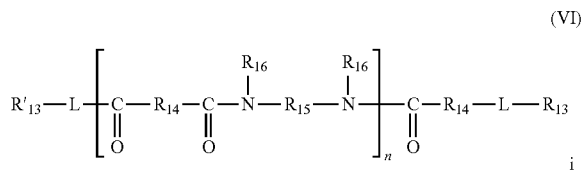

(VI)

in which:
- m denotes a whole number of amide units such that the number of ester groups represents from 10% to 50% of the total number of ester and amide groups;
- $R_{13}$ is independently in each case an alkyl or alkenyl group containing at least 4 carbon atoms and especially from 4 to 24 carbon atoms;
- $R_{14}$ represents independently in each case a $C_4$ to $C_{42}$ hydrocarbon-based group, on condition that 50% of the groups $R_{14}$ represent a $C_{30}$ to $C_{42}$ hydrocarbon-based group;
- $R_{15}$ represents independently in each case an organic group bearing at least two carbon atoms, hydrogen atoms and optionally one or more oxygen or nitrogen atoms;
- and $R_{16}$ represents independently in each case a hydrogen atom, a $C_1$ to $C_{10}$ alkyl group or a direct bond to $R_{15}$ or to another $R_{16}$ such that the nitrogen atom to which are attached both $R_3$ and $R_4$ forms part of a heterocyclic structure defined by $R_{16}$—N—$R_{15}$, with at least 50% of the groups $R_4$ representing a hydrogen atom.

In the particular case of formula (VI), the terminal fatty chains that are optionally functionalized for the purposes of the invention are terminal chains linked to the last nitrogen atom of the polyamide backbone.

In particular, the ester groups of formula (VI), which form part of the terminal and/or pendent fatty chains within the meaning of the invention, represent from 15% to 40% and better still from 20% to 35% of the total number of ester and amide groups.

Furthermore, m advantageously represents an integer ranging from 1 to 5 and better still greater than 2.

Preferably, $R_{13}$ is a $C_{12}$ to $C_{22}$ and preferably $C_{16}$ to $C_{22}$ alkyl group. Advantageously, $R_{14}$ can be a $C_{10}$ to $C_{42}$ hydrocarbon-based (alkylene) group. Preferably, at least 50% and better still at least 75% of the groups $R_2$ are groups containing from 30 to 42 carbon atoms. The other groups $R_2$ are $C_4$ to $C_{19}$ and even $C_4$ to $C_{12}$ hydrogenated groups.

Preferably, $R_{15}$ represents a $C_2$ to $C_{36}$ hydrocarbon-based group or a polyoxyalkylene group and $R_{16}$ represents a hydrogen atom. Preferably, $R_{15}$ represents a $C_2$ to $O_{12}$ hydrocarbon-based group.

The hydrocarbon-based groups may be linear, cyclic or branched, and saturated or unsaturated groups. Moreover, the alkyl and alkylene groups may be linear or branched, and saturated or unsaturated groups.

In general, the polymers of formula (VI) are in the form of mixtures of polymers, these mixtures also possibly containing a synthetic product corresponding to a compound of formula (VI) in which n is 0, i.e. a diester.

According to one particularly preferred form of the invention, use will be made of a mixture of copolymers of a $C_{36}$ diacid condensed onto ethylenediamine; the terminal ester groups result from the esterification of the remaining acid end groups with cetyl alcohol, stearyl alcohol or mixtures thereof (also known as cetylstearyl alcohol) (INCI name: Ethylenediamine/stearyl dimer dilinoleate copolymer). Its weight-average molecular mass is preferably 6000. These mixtures are especially sold by the company Arizona Chemical under the trade names Uniclear 80 and Uniclear 100 VG. They are sold, respectively, in the form of a gel at 80% (of active material) in a mineral oil, and at 100% (of active material). They have a softening point of 88° C. to 94° C.

As polyamide polycondensates corresponding to the general formula (VI), mention may also be made of polymers comprising at least one terminal fatty chain bonded to the polymer backbone via at least one tertiary amide bonding group (also known as an amide-terminated polyamide or ATPA). For further information regarding these polymers, reference may be made to U.S. Pat. No. 6,503,522.

According to one particularly preferred form of the invention, use will be made more particularly of a copolymer of hydrogenated linoleic diacid, of ethylenediamine and of di(C14-C18)alkylamine(s) (INCI name: Ethylenediamide/hydrogenated dimer dilinoleate copolymer bis-di-C14-C18 alkyl amide). This copolymer is especially sold under the trade name Sylvaclear A200V by the company Arizona Chemical.

According to another embodiment, the polyamide of formula (A) may also be an ester-terminated poly(esteramide) (ETPEA), for instance those whose preparation is described in U.S. Pat. No. 6,552,160.

According to one particularly preferred form of the invention, use will be made more particularly of a copolymer of hydrogenated linoleic diacid, of ethylenediamine and of neopentyl glycol and stearyl alcohol (INCI name: Bis-Stearyl Ethylenediamine/Neopentyl Glycol/Stearyl Hydrogenated Dimer Dilinoleate Copolymer). This copolymer is especially sold under the trade name Sylvaclear C75V by the company Arizona Chemical.

As polyamide polycondensates that may be used in the invention, mention may also be made of those comprising at least one terminal fatty chain bonded to the polymer backbone via at least one ether or polyether bonding group (it is then referred to as an ether-terminated poly(ether)amide). Such polymers are described, for example, in U.S. Pat. No. 6,399,713.

The polyamide in accordance with the invention advantageously has a softening point of greater than 65° C., which may be up to 190° C. It preferably has a softening point ranging from 70° C. to 130° C. and better still from 80° C. to 105° C. The polyamide is in particular a non-waxy polymer.

As polyamide polycondensates that may be used in the invention, mention may also be made of polyamide resins resulting from the condensation of an aliphatic dicarboxylic acid and a diamine (including compounds containing more than 2 carbonyl groups and 2 amine groups), the carbonyl and amine groups of adjacent individual units being condensed via an amide bond. These polyamide resins are especially the products sold under the brand name Versamid® by the companies General Mills, Inc. and Henkel Corp. (Versamid 930, 744 or 1655) or by the company Olin Mathieson Chemical Corp., under the brand name Onamid® especially Onamid S or C. These resins have a weight-average molecular mass ranging from 6000 to 9000. For further information regarding these polyamides, reference may be made to U.S. Pat. No. 3,645,705 and U.S. Pat. No. 3,148,125. Use is made more especially of Versamid® 930 or 744.

It is also possible to use the polyamides sold by the company Arizona Chemical under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209.

It is also possible to use vegetable-based polyamide resins, for instance those described in U.S. Pat. No. 5,783,657 and U.S. Pat. No. 5,998,570.

(7) Lipophilic polyurea or polyurethane polymers

As fatty-phase rheological agents, mention may also be made of polyurethanes and polyureas that are soluble or dispersible in hydrocarbon-based oil(s), and comprising:
- at least two urethane groups, at least two urea groups, or at least one urethane group and one urea group in the chain,
- at least one hydrocarbon-based long-chain, preferably branched, aliphatic polyester or hydrocarbon-based block or graft.

The expression "hydrocarbon-based long chain" means a linear or branched hydrocarbon-based chain containing at least 8 carbon atoms and preferably 10 to 500 carbon atoms.

The polymers that are preferred according to the invention are defined by one of the following three formulae (VII), (VIII) and (IX):

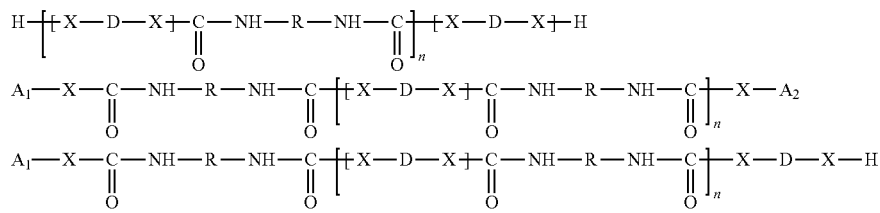

in which:

n denotes an integer from 1 to 10,000 and preferably from 1 to 1000,

X represents, separately or in combination, —O— or —NH—,

R is a divalent radical chosen from alkylene, cycloalkylene and aromatic radicals, and mixtures thereof, which are optionally functionalized, $A_1$ and $A_2$, which may be identical or different, denote linear, branched or cyclic monovalent hydrocarbon-based radicals, which are saturated or which may contain unsaturations, containing from 1 to 80 carbon atoms, D is 1) a saturated or unsaturated, aliphatic and/or cycloaliphatic hydrocarbon-based divalent block, and/or a hydrocarbon-based long-chain aliphatic polyester, 2) a graft

in which Z is a hydrocarbon-based trivalent radical which may contain one or more heteroatoms, and φ is a linear, branched or cyclic aliphatic chain, 3) mixtures of the blocks 1) and grafts 2).

The monovalent hydrocarbon-based radicals A1 and A2 are preferably chosen from saturated or unsaturated, aliphatic, cycloaliphatic and aromatic radicals. The radicals A1 and A2 are obtained from monoalcohols and/or monoamines optionally used to consume the isocyanate groups that are residual at the end of polymerization.

When D is a saturated or unsaturated, aliphatic and/or cycloaliphatic hydrocarbon-based block, it is obtained:
from a natural or synthetic oil,
from the product of addition (dimer, trimer or polymer) of at least two unsaturated aliphatic chains, such as aliphatic radicals derived from "dimeric" fatty acids, for instance the products of addition between oleic chains, or
from polyenes, which are preferably hydrogenated, such as polybutadiene, hydrogenated polyisoprene, or polyolefins or copolyolefins.

When D is a hydrocarbon-based long-chain aliphatic polyester block, it is preferably obtained from hydrocarbon-based long-chain branched polyesters such as, for example, poly(12-hydroxystearate).

When D is a graft, φ is a saturated or unsaturated, linear, branched or cyclic aliphatic chain comprising from 8 to 40 carbon atoms. The optional heteroatoms in the trivalent radical Z are preferably —O—, —N— and —S—.

The structuring polyurethanes and/or polyureas according to the invention result from the polymerization reaction between:

1) at least one aliphatic, cycloaliphatic and/or aromatic diisocyanate of general formula O=C=N—R—N=C=O, in which R is as defined above, 2) at least one difunctional derivative HX-D-XH, having two active hydrogens which can each react with an isocyanate group, in which
X denotes —O— or —NH—, and
D is as defined above, and 3) optionally, a monofunctional derivative $A_1$-XH, or two monofunctional derivatives $A_1$-XH and $A_2$-XH, having only one active hydrogen which can react with an isocyanate group, to consume the residual isocyanate groups that have not fully reacted with the difunctional reagents H—X-D-X—H, the monofunctional derivatives $A_1$-XH and $A_2$-XH possibly being identical or different, and $A_1$ and $A_2$ being as defined above.

The isocyanates used in the polymerization reaction may be aliphatic, cycloaliphatic or aromatic. Hexamethylene diisocyanate, isophorone diisocyanate, toluene diisocyanate or 4,4'-dicyclohexylmethane diisocyanate will be advantageously used.

The difunctional derivatives H—X-D-X—H may be chosen from diol dimers and derivatives thereof, alkanediols, polydienes with hydroxyl ends, which are preferably hydrogenated, polyolefins with hydroxyl ends, long-alkyl-chain branched polyesters bearing at least two reactive groups, natural or synthetic oils bearing two or three hydroxyl groups, and finally long-aliphatic-chain diamines and diamine dimers.

The diol dimers are branched $C_{36}$ aliphatic and/or alicyclic diols, and/or a mixture of the said dimers. These diols are prepared from the "corresponding dimeric fatty acids".

The expression "corresponding dimeric fatty acids" means dimeric fatty acids which have the same structure as these diols, but which have two carboxylic acid ends instead of diol ends. The conversion of the dimeric fatty acids into diol dimers may be carried out either by hydrogenation of methyl esters of the dimeric fatty acids or by direct dimerization of oleyl alcohol. Mention will be made in particular of the diol dimers sold by the company Cognis under the trade names Sovermol 908 (at 97% purity) and Sovermol 650 NS (at 68% purity).

It is also possible to use polyether diol oligomers and polycarbonate diol oligomers, prepared by subsequent etherification or esterification of these same branched C36 diol dimers. These oligomers generally have a number-average molecular mass in the region of from 500 to 2000, and contain two hydroxyl functions.

The polydienes with hydroxyl end groups are, for example, those defined in French patent FR-2 782 723. They are chosen from the group comprising polybutadiene, polyisoprene and poly(1,3-pentadiene) homopolymers and copolymers. These oligomers have a number-average molecular mass of less than 7000, preferably ranging from 1000 to 5000. They have chain-end functionality of from 1.8 to 3 and preferably in the region of 2. These polydienes bearing hydroxyl end groups are, for example, the hydroxylated polybutadienes sold by the company Elf Atochem under the brand names Poly BD-45H® and Poly BD R-20 LM®. These products are preferably used hydrogenated.

It is also possible to use polyolefin homopolymers or copolymers with α,ω-hydroxyl ends, such as, for example:
polyisobutylene oligomers with α,ω-hydroxyl ends, or
the copolymers sold by the company Mitsubishi under the brand name Polytail®, in particular those of formula (X) below:

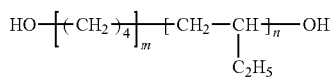

with a melting point of 60 to 70° C.

It is possible to use as difunctional derivative H—X-D-X—H, a long-alkyl-chain branched polyester comprising at least two reactive groups, such as, for example, poly(12-hydroxystearate) containing hydroxyl ends. This polyester is obtained by self-condensation of 1,2-hydroxystearic acid, followed by reaction with a polyol to consume the residual acid groups. This oligomer of formula (XI):

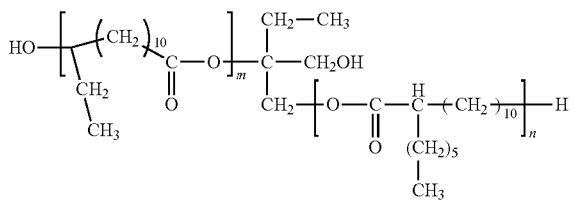

in which the sum m+n is such that the oligomer has a number-average molecular mass in the region of 2000 and a hydroxyl functionality in the region of 1.8.

Natural or synthetic oils bearing 2 or 3 hydroxyl groups may also be used as difunctional derivative H—X-D-X—H.

In one particular embodiment of the invention, the oils used will be those bearing two hydroxyl groups per chain, and preferably the monoglycerides of structure:

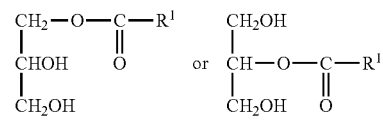

$R^1$ being a linear or branched $C_8$ to $C_{30}$ alkyl chain such as, for example, glyceryl monostearate.

Such glyceryl monoesters correspond, for example, to the difunctional derivatives H—X-D-X—H, in which:

D represents

X represents —O—, and

represents

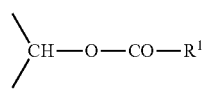

in which $R_1$ is defined as above.

When these glycerol monoesters are reacted with a diisocyanate, a solubilizing graft is introduced into the polymer chain rather than a block, as was the case with the difunctional derivatives mentioned above.

In one variant, a difunctional derivative H—X-D-X—H chosen from oils bearing three hydroxyl groups per chain, such as, for example, hydrogenated or non-hydrogenated castor oil, will be used.

In this case, the polymerization reaction is carried out with a deficit of diisocyanate relative to the reaction stoichiometry, to avoid the crosslinking of the polymer and to conserve good solubility thereof.

Long-aliphatic-chain diols may also be used. Advantageously, diols of structure HO-D-OH in which D is a linear or branched alkyl chain containing from 8 to 40 carbon atoms will be used. These diols are sold by the company Atochem under the name Vikinol®. Mention will also be made of 1,12-dodecanediol and 1,10-decanediol, the latter being sold by the company Cognis under the trade name Sovermol 110®.

It is also possible to use diols of structure

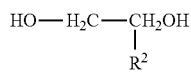

in which $R_2$ is an alkyl chain containing from 8 to 40 carbon atoms.

These long-aliphatic-chain diols are preferably used with any one of the H—X-D-X—H derivatives mentioned above, to serve as chain couplers during the synthesis of polyurethanes and/or polyureas.

Finally, long-aliphatic-chain diamines or diamine dimers may be used as difunctional derivative H—X-D-X—H.

The use of such reagents in the polymerization reaction makes it possible to introduce into the polymer urea groups rather than urethane groups.

According to one particular embodiment of the invention, diamine dimers having the same structure as the diol dimers mentioned above will be used, that is to say diamine dimers comprising two primary amine functions instead of hydroxyl groups.

These diamine dimers may be obtained from the conversion of dimeric fatty acids, like the diol dimers.

In one variant, diamines of structure $H_2N$-D-$NH_2$ in which D is a linear or branched alkyl chain containing from 8 to 40 carbon atoms may be used. These diamines are preferably used as a mixture with a difunctional derivative H—X-D-X—H chosen from diol dimers and derivatives thereof, polydienes and polyolefins with hydroxyl ends, long-alkyl-chain branched polyesters, and oils bearing 2 or 3 hydroxyl groups, mentioned above.

Among these diamines, mention may be made of:
1,10-diaminodecane and 1,12-diaminododecane, and
the following diamine oils sold by the company Akzo Nobel: cocopropylene diamine (distilled or undistilled) Duomeen® C or CD, hydrogenated tallowpropylene diamine Duomeen® HT, C16-22 alkylpropylene diamine Duomeen® M, oleylpropylene diamine Duomeen® O, tallowpropylene diamine Duomeen® T.

As regards the monofunctional derivatives $A_1$-XH and $A_2$-XH, they are advantageously chosen from monoalcohols and monoamines with linear or branched alkyl chains containing from 1 to 80 carbon atoms, natural or synthetic oils bearing a single hydroxyl group per chain, such as, for example, glycerol diesters or citric acid triesters of a fatty alcohol.

The polycondensation reactions envisaged are conventionally carried out in an organic solvent capable of dissolving the reagents and the polymer formed. This solvent is preferably readily removable at the end of the reaction, in particular by distillation, and does not react with the isocyanate groups.

Generally, each of the reagents is dissolved in some of the organic solvent before the polymerization reaction.

It is occasionally desired to use a catalyst to activate the polymerization. This catalyst will generally be chosen from the catalysts commonly used in polyurethane and polyurea chemistry, such as, for example, tin 2-ethylhexanoate.

The molar proportion between the main reagents of the polymerization reaction depends on the chemical structure and on the molecular weight of the polymers (polyurethanes and/or polyureas) which it is desired to obtain, as is conventionally the case in polyurethane and polyurea chemistry. Similarly, the order of introduction of the reagents will be adapted to this chemistry.

Thus, the reaction of two moles of functional derivative H—X-D-X—H with one mole of diisocyanate gives, after total consumption of the reagents, a polymer defined by formula (XII):

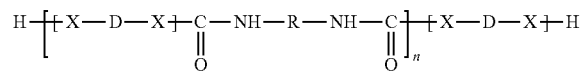

For this reaction, the process will advantageously be performed in the following manner:
the initial medium is a solution comprising two moles of derivative H—X-D-X—H, for example two moles of diol dimer, in a solvent, for example tetrahydrofuran,
a solution comprising one mole of diisocyanate dissolved in the same solvent, such as, for example, toluene diisocyanate dissolved in tetrahydrofuran, is added dropwise to this initial solution.

Moreover, the equimolar reaction of a difunctional derivative H—X-D-X—H with a diisocyanate, with consumption of the residual isocyanates by a monofunctional compound A1-XH, gives a polymer defined by formula (XIII):

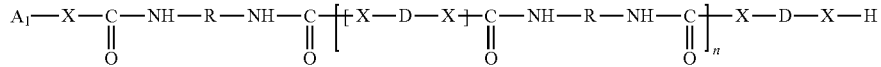

This reaction will then preferably be carried out by simultaneous addition, into a reactor, of an organic solution of one mole of H—X-D-X—H, such as, for example, a Polytail® described above, and of an organic solution of one mole of diisocyanate, for instance 4,4'-dicyclohexylmethane diisocyanate. The simultaneous addition of these two organic solutions is also known as "double addition". At the end of the double addition, the reaction mixture is heated at 60° C. for 5 hours. A sample of the reaction medium is then taken to assay the residual isocyanates using a method known to those skilled in the art. Finally, a solution of a chosen monofunctional compound A1-X—H is added to the reaction medium, in an amount which is sufficient to consume the residual isocyanates, this amount having been estimated from the assay of the residual isocyanates. 1-Decanol will advantageously be used as monofunctional derivative A1-X—H.

Finally, the reaction between
one mole of compound H—X-D-X—H, such as, for example, a diol dimer,
three moles of diisocyanate such as, for example, 4,4'-dicyclohexylmethane diisocyanate, and
two moles of coupler of structure

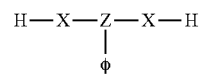

in which φ is a linear, branched or cyclic aliphatic chain comprising from 8 to 20 carbon atoms, leads to the formation of a polymer that is in both block and grafted form, of structure:

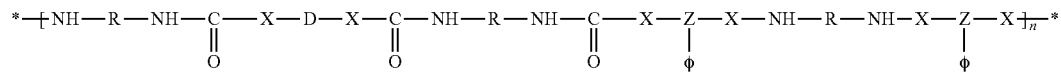

Any residual isocyanates may be consumed by adding a suitable amount of monofunctional reagent A1-X—H.

To obtain such a polymer, the process is performed in the following manner:
  the initial reaction medium consists of a solution comprising one mole of a difunctional derivative H—X-D-X—H,
  a solution of three moles of diisocyanate is added dropwise to this medium,
  the mixture is then left to react for 3 hours at 60° C.,
  next, an organic solution comprising two moles of a coupler defined by the formula:

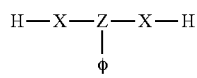

Any residual isocyanates may be consumed by adding a suitable amount of monofunctional reagent A1-X—H.

(8) Block Polymers

It is also possible to use, as fatty-phase rheological agent, grafted-block or block polymers.

Grafted-block or block copolymers that may be mentioned include those comprising at least one block resulting from the polymerization of at least one ethylenic monomer containing one or more optionally conjugated ethylenic bonds, for instance ethylene or dienes such as butadiene and isoprene, and of at least one block of a vinyl polymer and better still a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these polymers that may be mentioned are block copolymers, especially of "diblock" or "triblock" type such as polystyrene/polyisoprene (SI), polystyrene/polybutadiene (SB) such as those sold under the name Luvitol HSB by BASF, of the type such as polystyrene/copoly(ethylene-propylene) (SEP) such as those sold under the name "Kraton" by Shell Chemical Co. or of the type such as polystyrene/copoly-(ethylene-butylene) (SEB). Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) and Kraton D-1107 (SIS) may be used in particular. The polymers are generally known as hydrogenated or non-hydrogenated diene copolymers.

Gelled Permethyl 99A-750, 99A-753-59 and 99A-753-58 (mixture of triblock and of star polymer), Versagel 5960 from Penreco (triblock+star polymer); OS129880, OS129881 and OS84383 from Lubrizol (styrene/(meth)acrylate copolymer) may also be used.

As grafted-block or block copolymers comprising at least one block resulting from the polymerization of at least one ethylenic monomer containing one or more ethylenic bonds and of at least one block of an acrylic polymer, mention may be made of poly(methyl methacrylate)/polyisobutylene diblock or triblock copolymers or grafted copolymers containing a poly(methyl methacrylate) backbone and polyisobutylene grafts.

As grafted-block or block copolymers comprising at least one block resulting from the polymerization of at least one ethylenic monomer containing one or more ethylenic bonds and of at least one block of a polymer such as a $C_2$-$C_{18}$ polyalkylene (especially polyoxyethylene and/or polyoxypropylene), mention may be made of polyoxyethylene/polybutadiene or polyoxyethylene/polyisobutylene diblock or triblock copolymers.

(9) Cholesterol-based Liquid-crystal Agents

The term "liquid-crystal agents" means compounds that generate a mesomorphic state, i.e. a state for which melting of the crystals affords liquids that have optical properties comparable to those of certain crystals. These compounds are more specifically defined in the chapter Liquid Crystals in Ullmann's encyclopaedia.

These liquid-crystal agents are described in particular in the patents or patent applications EP 545 409, WO 94/109 086, EP 709 445, GB 2 282 145, GB 2 276 883, WO 95/132247, WO 95/132248, EP 686 674 and EP 711 780.

These liquid-crystal agents may react in response to the vibrations by a change in viscosity and/or by a change in colour. More particularly, the compounds that generate a mesomorphic state are compounds containing a cholesterol-based function, the structure of which is as follows:

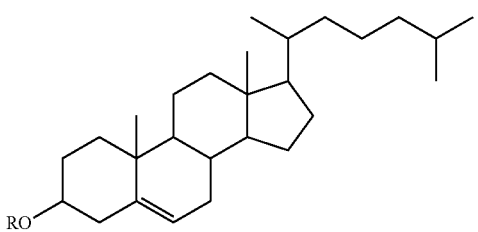

R is an alkyl or alkylcarbonyl group containing from 1 to 30 carbon atoms optionally substituted with cyclic, aromatic groups, halogens, branched or unbranched.

In a non-limiting manner, liquid-crystal agents corresponding to this definition that may be mentioned include: cholesteryl erucyl carbonate, cholesteryl methyl carbonate, cholesteryl oleyl carbonate, cholesteryl para-nonyl phenyl carbonate, cholesteryl phenyl carbonate, cholesteryl acetate, cholesteryl benzoate, cholesteryl butyrate, cholesteryl isobutyrate, cholesteryl chloride, cholesteryl chloroacetate, cholesteryl cinnamate, cholesteryl crotonate, cholesteryl decanoate, cholesteryl erucate, cholesteryl heptanoate, cholesteryl hexanoate, cholesteryl myristate, cholesteryl nonanoate, cholesteryl octanoate, cholesteryl oleate, cholesteryl propionate, cholesteryl valerate and dicholesteryl carbonate.

Among the oil-phase thickening or gelling rheological agents as listed previously, use will be made more particularly of:
- semicrystalline polymers, in particular semicrystalline polymers derived from a crystallizable-chain monomer chosen from saturated $C_{14}$ to $C_{22}$ alkyl (meth)acrylates and more particularly poly(stearyl acrylate) or poly (behenyl acrylate).
- lipophilic polyamide polycondensates
- mixtures thereof.

Among these thickeners, use will be made even more preferentially of semicrystalline polymers, in particular semicrystalline polymers derived from a crystallizable-chain monomer chosen from saturated $C_{14}$ to $C_{22}$ alkyl (meth) acrylates and more particularly poly(stearyl acrylate) or poly(behenyl acrylate).

In particular, use will be made more of the semicrystalline polymers having the INCI name "Poly C10-30 alkyl acrylate", for instance the Intelimer® products from the company Air Products, for instance the product Intelimer® IPA 13-1, which is a polystearyl acrylate, or the product Intelimer® IPA 13-6, which is a behenyl polymer.

Photoprotective System

According to the invention, the photoprotective system may consist of one or more lipophilic or insoluble organic UV-screening agents and/or one or more mineral UV-screening agents. It will preferentially consist of at least one lipophilic organic UV-screening agent.

The term "lipophilic organic UV-screening agent" means any organic UV-screening agent that can be fully dissolved in molecular state in a liquid aqueous phase or that can be dissolved in colloidal form (for example in micellar form) in a liquid fatty phase.

The term "insoluble organic UV-screening agent" means any organic UV-screening agent that may be in the form of particles in a liquid fatty phase.

The lipophilic or insoluble organic UV-screening agents are chosen especially from cinnamic derivatives; anthranilates; salicylic derivatives; dibenzoylmethane derivatives, camphor derivatives; benzophenone derivatives; β, β-diphenylacrylate derivatives; triazine derivatives; benzotriazole derivatives; benzalmalonate derivatives, especially those mentioned in U.S. Pat. No. 5,624,663; imidazolines; p-aminobenzoic acid (PABA) derivatives; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanin derivatives such as those described in patent applications WO 04/006 878, WO 05/058 269 and WO 06/032 741; and mixtures thereof.

As examples of additional organic photoprotective agents, mention may be made of those denoted hereinbelow under their INCI name:

As examples of lipophilic or insoluble organic UV-screening agents, mention may so be made of those denoted below under their INCI name:

Dibenzoylmethane Derivative:
Butylmethoxydibenzoylmethane or avobenzone sold under the trade name Parsol 1789 by the company DSM Nutritional Products,
Para-Aminobenzoic Acid Derivatives:
PABA,
Ethyl PABA,
Ethyl dihydroxypropyl PABA,
Ethylhexyl dimethyl PABA sold in particular under the name Escalol 507 by ISP,
Salicylic Derivatives:
Homosalate sold under the name Eusolex HMS by Rona/EM Industries,
Ethylhexyl salicylate sold under the name Neo Heliopan OS by Symrise,
Cinnamic Derivatives:
Ethylhexyl methoxycinnamate sold especially under the trade name Parsol MCX by DSM Nutritional Products,
Isopropyl methoxycinnamate,
Isoamyl methoxycinnamate sold under the trade name Neo Heliopan E 1000 by
Symrise,
Cinoxate,
Diisopropyl methylcinnamate,
β,β-Diphenylacrylate Derivatives:
Octocrylene sold especially under the trade name Uvinul N539 by BASF,
Etocrylene, sold especially under the trade name Uvinul N35 by BASF,
Benzophenone Derivatives:
Benzophenone-1 sold under the trade name Uvinul 400 by BASF,
Benzophenone-2 sold under the trade name Uvinul D50 by BASF,
Benzophenone-3 or oxybenzone sold under the trade name Uvinul M40 by BASF,
Benzophenone-6 sold under the trade name Helisorb 11 by Norquay,
Benzophenone-8 sold under the trade name Spectra-Sorb UV-24 by American Cyanamid,
Benzophenone-12
N-hexyl 2-(4-diethylamino-2-hydroxybenzoyl)benzoate sold under the trade name Uvinul A+ or in the form of a mixture with octyl methoxycinnamate under the trade name Uvinul A+B by BASF,
1,1'-(1,4-piperazinediyl)bis[1-[2-[4-(diethylamino)-2-hydroxybenzoyl]phenyl]methanone (CAS 919803-06-8) in micronized or non-micronized form,
Benzylidenecamphor Derivatives:
3-Benzylidenecamphor manufactured under the name Mexoryl SD by Chimex,
4-Methylbenzylidenecamphor sold under the name Eusolex 6300 by Merck,
Polyacrylamidomethylbenzylidenecamphor manufactured under the name "Mexoryl SW" by Chimex.
Phenylbenzotriazole Derivatives:
Drometrizole trisiloxane sold under the name Silatrizole by Rhodia Chimie,
Methylenebis(benzotriazolyl)tetramethylbutylphenol sold in solid form under the trade name MIXXIM BB/100 by Fairmount Chemical, or in micronized form as an aqueous dispersion under the trade name Tinosorb M by BASF,
Triazine Derivatives:
bis-Ethylhexyloxyphenol methoxyphenyl triazine sold under the trade name Tinosorb S by BASF,
Ethylhexyl triazone sold in particular under the trade name Uvinul T150 by BASF, Diethylhexyl butamido triazone sold under the trade name Uvasorb HEB by Sigma 3V,
2,4,6-Tris(diisobutyl 4'-aminobenzalmalonate)-s-triazine,
2,4,6-Tris(dineopentyl 4'-aminobenzalmalonate)-s-triazine,
2,4-Bis(dineopentyl 4'-aminobenzalmalonate)-6-(n-butyl 4'-aminobenzoate)-s-triazine;
2,4-Bis(n-butyl 4'-aminobenzoate)-6-[(3-{1,3,3,3-tetramethyl-1-[(trimethylsilyl)oxy]-disiloxanylpropyl)amino]-s-triazine,
the symmetrical triazine screening agents described in U.S. Pat. No. 6,225,467, patent application WO 2004/085412 (see compounds 6 and 9) or the document "Symmetrical Triazine Derivatives" IP.COM Journal, IP.COM INC West Henrietta, N.Y., US (20 Sep. 2004), especially 2,4,6-tris(biphenyl)-1,3,5-triazines (in particular 2,4,6-tris (biphenyl-4-yl)-1,3,5-triazine) and 2,4,6-tris(terphenyl)-1,3,5-triazine which is also mentioned in Beiersdorf patent applications WO 06/035000, WO 06/034982, WO 06/034991, WO 06/035007, WO 2006/034992 and WO 2006/034985.
Anthranilic Derivatives:
Menthyl anthranilate sold under the trade name Neo Heliopan MA by Symrise,
Imidazoline Derivatives:
Ethylhexyl dimethoxybenzylidene dioxoimidazoline propionate,
Benzalmalonate Derivatives:
Dineopentyl 4'-methoxybenzalmalonate
Polyorganosiloxane containing benzalmalonate functions, for instance Polysilicone-15, sold under the trade name Parsol SLX by DSM,
4,4-Diarylbutadiene Derivatives:
1,1-dicarboxy(2,2'-dimethylpropyl)-4,4-diphenylbutadiene
Benzoxazole Derivatives:
2,4-Bis[5-1(dimethylpropyl)benzoxazol-2-Yl-(4-phenyl) imino]-6-(2-ethylhexyl)imino-1,3,5-triazine, sold under the name of Uvasorb K2A by Sigma 3V,
and mixtures thereof.
Lipophilic Merocyanin Derivatives:
Octyl 5-N,N-diethylamino-2-phenylsulfonyl-2,4-pentadienoate and mixtures thereof.
The preferential liposoluble or insoluble organic screening agents are chosen from:
Butylmethoxydibenzoylmethane
Ethylhexyl Methoxycinnamate,
Ethylhexyl salicylate,
Homosalate,
Butylmethoxydibenzoylmethane,
Octocrylene,
Benzophenone-3,
n-Hexyl 2-(4-diethylamino-2-hydroxybenzoyl)benzoate,
4-Methylbenzylidenecamphor,
Methylenebis(benzotriazolyl)tetramethylbutylphenol,
Bis(ethylhexyloxyphenyl)methoxyphenyltriazine
Ethylhexyl triazone,
Diethylhexyl butamido triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4,6-Tris(biphenyl-4-yl)-1,3,5-triazine,
2,4,6-Tris(terphenyl)-1,3,5-triazine,
Drometrizole trisiloxane
Polysilicone-15,
1,1-dicarboxy(2,2'-dimethylpropyl)-4,4-diphenylbutadiene
2,4-bis[5-1(Dimethylpropyl)benzoxazol-2-yl(4-phenyl) imino]-6-(2-ethylhexyl)imino-1,3,5-triazine,
and mixtures thereof.
The preferential lipophilic organic screening agents are chosen from:
Butylmethoxydibenzoylmethane,
Octocrylene,
Ethylhexyl salicylate,
Bis(ethylhexyloxyphenyl)methoxyphenyltriazine
Ethylhexyl triazone,
Diethylhexyl butamido triazone,
Drometrizole trisiloxane, and mixtures thereof.

The mineral UV-screening agents used in accordance with the present invention are metal oxide pigments. More preferentially, the mineral UV-screening agents of the invention are metal oxide pigments with a mean elemental particle size of less than or equal to 500 nm, more preferentially between 5 nm and 500 nm and even more preferentially between 10 nm and 100 nm, and preferentially between 15 and 50 nm.

They may be chosen especially from titanium oxide, zinc oxide, iron oxide, zirconium oxide and cerium oxide, or mixtures thereof, and more particularly titanium oxides.

Such coated or uncoated metal oxide pigments are described in particular in patent application EP-A-0 518 773. Commercial pigments that may be mentioned include the products sold by the companies Kemira, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
  with silica, such as the product Sunveil from the company Ikeda,
  with silica and iron oxide, such as the product Sunveil F from the company Ikeda,
  with silica and alumina, such as the products Microtitanium Dioxide MT 500 SA and Microtitanium Dioxide MT 100 SA from the company Tayca and Tioveil from the company Tioxide,
  with alumina, such as the products Tipaque TTO-55 (B) and Tipaque TTO-55 (A) from the company Ishihara and UVT 14/4 from the company Kemira,
  with alumina and aluminium stearate, such as the product Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck,
  with silica, alumina and alginic acid, such as the product MT-100 AQ from the company Tayca,
  with alumina and aluminium laurate, such as the product Microtitanium Dioxide MT 100 S from the company Tayca,
  with iron oxide and iron stearate, such as the product Microtitanium Dioxide MT 100 F from the company Tayca,
  with zinc oxide and zinc stearate, such as the product BR351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF TiO2SI3 by the company Cardre, anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wacker under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:
those sold under the name Z-Cote by the company Sunsmart;
those sold under the name Nanox by the company Elementis;
those sold under the name Nanogard WCD 2025 by the company Nanophase Technologies.

The coated zinc oxide pigments are, for example:
those sold under the name Zinc Oxide CS-5 by the company Toshibi (ZnO coated with polymethylhydrogenosiloxane);
those sold under the name Nanogard Zinc Oxide FN by the company Nanophase Technologies (as a 40% dispersion in Finsolv TN, $C_{12}$-$C_{15}$ alkyl benzoate);
those sold under the name Daitopersion ZN-30 and Daitopersion ZN-50 by the company Daito (dispersions in cyclopolymethylsiloxane/oxyethylenated polydimethylsiloxane, containing 30% or 50% of nanozinc oxides coated with silica and polymethylhydrogenosiloxane);
those sold under the name "NFD Ultrafine ZnO" by the company Daikin (ZnO coated with perfluoroalkyl phosphate and copolymer based on perfluoroalkylethyl as a dispersion in cyclopentasiloxane);
those sold under the name SPD-Z1 by the company Shin-Etsu (ZnO coated with silicone-grafted acrylic polymer, dispersed in cyclodimethylsiloxane);
those sold under the name Escalol Z100 by the company ISP (alumina-treated ZnO dispersed in an ethylhexyl methoxycinnamate/PVP-hexadecene copolymer/methicone mixture);
those sold under the name Fuji ZnO-SMS-10 by the company Fuji Pigment (ZnO coated with silica and polymethylsilsesquioxane);
those sold under the name Nanox Gel TN by the company Elementis (ZnO dispersed at a concentration of 55% in C12-C15 alkyl benzoate with hydroxystearic acid polycondensate).

The uncoated cerium oxide pigments are sold under the name Colloidal Cerium Oxide by the company Rhone-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220, The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, especially of titanium dioxide and of cerium dioxide, including the silica-coated equal-weight mixture of titanium dioxide and of cerium dioxide, sold by the company Ikeda under the name Sunveil A, and also the alumina, silica and silicone-coated mixture of titanium dioxide and of zinc dioxide, such as the product M 261 sold by the company Kemira, or the alumina, silica and glycerol-coated mixture of titanium dioxide and of zinc dioxide, such as the product M 211 sold by the company Kemira.

According to the invention, coated or uncoated titanium oxide pigments are particularly preferred.

The photoprotective system according to the invention is preferably present in the compositions according to the invention in a content ranging from 0.1% to 40% by weight and in particular from 5% to 25% by weight relative to the total weight of the composition.

Matting Agents

The term "matting agent" means agents intended to make the skin visibly more matt and less shiny.

The matting effect of the agent and/or composition containing it may especially be evaluated using a gonioreflectometer, by measuring the ratio R between the specular reflection and the scattered reflection. A value of R of less than or equal to 2 generally indicates a matting effect.

The matting agent may especially be chosen from a rice starch or a corn starch: INCI name: *Zea mays* (Corn) Starch, such as, in particular, the product sold under the trade name Farmal CS 3650 Plus 036500 by National Starch, kaolinite, talc, a pumpkin seed extract, cellulose microbeads, plant fibres, synthetic fibres, in particular polyamide fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles and especially mixed silicate particles, and mixtures thereof.

Examples of matting agents that may especially be mentioned include:
rice or corn starch, in particular an aluminium starch octenyl succinate sold under the name Dry Flo® by the company National Starch;
kaolinite;
silicas;
talc;

- a pumpkin seed extract as sold under the name Curbilene® by the company Indena;
- cellulose microbeads as described in patent application EP 1 562 562;
- fibres, such as silk fibre, cotton fibre, wool fibre, flax fibre, cellulose fibre extracted especially from wood, from vegetables or from algae, polyamide fibre (Nylon®), modified cellulose fibre, poly-p-phenyleneterephthamide fibre, acrylic fibre, polyolefin fibre, glass fibre, silica fibre, aramid fibre, carbon fibre, Teflon® fibre, insoluble collagen fibre, polyester fibre, polyvinyl chloride or polyvinylidene chloride fibre, polyvinyl alcohol fibre, polyacrylonitrile fibre, chitosan fibre, polyurethane fibre, polyethylene phthalate fibre, fibres formed from a mixture of polymers, resorbable synthetic fibres, and mixtures thereof described in patent application EP 1 151 742;
- expanded acrylic copolymer microspheres such as those sold by the company Expancel under the name Expancel 551®;
- fillers with an optical effect as described in patent application FR 2 869 796, in particular:
- polyamide (Nylon®) powders, for instance particles of Nylon 12 such as Orgasol from Arkema with a mean size of 10 microns and a refractive index of 1.54,
- silica powders, for instance Silica beads SB150 from Miyoshi with a mean size of 5 microns and a refractive index of 1.45,
- polytetrafluoroethylene powders, for instance PTFE Ceridust 9205F from Clariant, with a mean size of 8 microns and a refractive index of 1.36,
- silicone resin powders, for instance the silicone resin Tospearl 145A from GE Silicone with a mean size of 4.5 microns and a refractive index of 1.41,
- acrylic copolymer powders, especially of polymethyl (meth)acrylate, for instance the PMMA particles Jurymer MBI from Nihon Junyoki, with a mean size of 8 microns and a refractive index of 1.49, or the Micropearl M100@ and F 80 ED® particles from the company Matsumoto Yushi-Seiyaku,
- wax powders, for instance the paraffin wax particles Microease 114S from Micropowders, with a mean size of 7 microns and a refractive index of 1.54,
- polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns and a refractive index of 1.48),
- silicone resin powders, for instance Silicon Resin Tospearl® 145 A DE GE silicone with a mean size of 4.5 µm,
- elastomeric crosslinked organopolysiloxane powders coated with silicone resin, especially with silsesquioxane resin, as described, for example, in U.S. Pat. No. 5,538,793. Such elastomer powders are sold under the names KSP-100, KSP-101, KSP-102, KSP-103, KSP-104 and KSP-105 by the company Shin-Etsu, and
- talc/titanium dioxide/alumina/silica composite powders, such as those sold under the name Coverleaf® AR-80 by the company Catalyst & Chemicals,
- mixtures thereof,
- compounds that absorb and/or adsorb sebum as described in patent application FR 2 869 796. Mention may be made especially of:
- silica powders, for instance the porous silica microspheres sold under the name Silica Beads SB-700 sold by the company Miyoshi, the products Sunsphere® H51, Sunsphere® H33 and Sunsphere® H53 sold by the company Asahi Glass; the polydimethylsiloxane-coated amorphous silica microspheres sold under the name SA Sunsphere® H-33 and SA Sunsphere® H-53 sold by the company Asahi Glass;
- amorphous mixed silicate powders, especially of aluminium and magnesium, for instance the product sold under the name Neusilin UFL2 by the company Sumitomo;
- polyamide (Nylon®) powders, for instance Orgasol® 4000 sold by the company Arkema, and
- acrylic polymer powders, especially of polymethyl methacrylate, for instance Covabead® LH85 sold by the company Wackherr; of polymethyl methacrylate/ethylene glycol dimethacrylate, for instance Dow Corning 5640 Microsponge® Skin Oil Adsorber sold by the company Dow Corning, or Ganzpearl® GMP-0820 sold by the company Ganz Chemical; of polyallyl methacrylate/ethylene glycol dimethacrylate, for instance Poly-Pore® L200 or Poly-Pore® E200 sold by the company Amcol; of ethylene glycol dimethacrylate/lauryl methacrylate copolymer, for instance Polytrap® 6603 sold by the company Dow Corning;
- silicate particles, such as alumina silicate;
- mixed silicate particles, such as:
- magnesium aluminium silicate particles, such as saponite or hydrated magnesium aluminium silicate with a sodium sulfate sold under the trade name Sumecton® by the company Kunimine;
- the magnesium silicate, hydroxyethylcellulose, black cumin oil, marrow oil and phospholipids complex or Matipure® from Lucas Meyer, and
- mixtures thereof.

Preferred matting agents that may preferably be used according to the invention include an extract of pumpkin seeds, a rice or corn starch, kaolinite, silicas, talc, polyamide powders, polyethylene powders, acrylic copolymer powders, expanded acrylic copolymer microspheres, silicone resin microbeads, mixed silicate particles, and mixtures thereof, and more preferentially talc.

The matting agent(s) are preferably in contents ranging from 10% to 40% by weight and even more preferentially from 15% to 25% by weight relative to the total weight of the composition.

Oily Phase

The compositions according to the invention generally comprise an oily phase containing at least one hydrocarbon-based oil and/or one silicone oil such as those mentioned previously.

As oils that may be present in the fatty phase of the compositions of the invention, mention may be made of mineral oils (paraffin); plant oils (sweet almond oil, *macadamia* oil, blackcurrant pip oil or jojoba oil); fatty alcohols, fatty amides (such as isopropyl lauroyl sarcosinate sold under the name Eldew SL-205 by the company Ajinomoto), fatty acids or esters (for instance the $C_{12}$-$C_{15}$ alkyl benzoate sold under the trade name Finsolv TN or Witconol TN by the company Witco isopropyl lanolate, triglycerides, including capric/caprylic acid triglycerides, the dicaprylyl carbonate sold under the name Cetiol CC by the company Cognis), oxyethylenated or oxypropylenated fatty esters and ethers; silicone oils (cyclomethicone or polydimethylsiloxanes (PDMS)), fluoro oils and polyalkylenes.

The oily phase preferably represents from 15% to 60% by weight and more preferentially from 20% to 50% by weight relative to the total weight of the composition.

Additives

The aqueous compositions in accordance with the present invention may also comprise standard cosmetic adjuvants chosen especially from softeners, stabilizers, emollients, antifoams, fragrances, essential oils, lipophilic active agents, lipophilic dyes, insect repellents, preserving agents, waxes, polymers or any other ingredient usually used in cosmetics and/or dermatology.

Needless to say, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

Among the lipophilic cosmetic active agents, examples that may be mentioned include antioxidants, keratolytic agents such as N-alkylsalicylic acids, for example N-octanoyl-5-salicylic acid; vitamins, for instance vitamin E (tocopherol and derivatives), vitamin A (retinol and derivatives); softeners and any lipophilic active agent usually used for caring for the skin or the hair.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C.

Use may be made especially of hydrocarbon-based waxes such as beeswax, lanolin wax and Chinese insect waxes; rice wax, carnauba wax, ouricurry wax, esparto grass wax, cork fibre wax, sugarcane wax, Japan wax and sumach wax; montan wax, microcrystalline waxes, paraffin waxes; polyethylene waxes, the waxes obtained by Fisher-Tropsch synthesis, and waxy copolymers, and also esters thereof.

Mention may also be made of waxes obtained by catalytic hydrogenation of animal or plant oils containing linear or branched C8-C32 fatty chains.

Among these waxes, mention may especially be made of hydrogenated jojoba oil, hydrogenated sunflower oil, hydrogenated castor oil, hydrogenated coconut oil, hydrogenated lanolin oil and bis(1,1,1-trimethylolpropane)tetrastearate sold under the name Hest 2T-4S by the company Heterene, bis(1,1,1-trimethylolpropane)tetrabehenate sold under the name Hest 2T-4B by the company Heterene.

Mention may also be made of fluoro waxes.

Use may also be made of the wax obtained by hydrogenation of olive oil esterified with stearyl alcohol, sold under the name Phytowax Olive 18L57, or the waxes obtained by hydrogenation of castor oil esterified with cetyl alcohol, sold under the names Phytowax Ricin 16L64 and 22L73 and by the company Sophim. Such waxes are described in patent application FR-A-2 792 190.

According to one particularly preferred form of the invention, the following will be chosen:
(i) polyolefin waxes derived from the polymerization and especially the homopolymerization of α-olefin corresponding to the general formula R—CH—CH$_2$ in which R denotes an alkyl radical, preferably a linear alkyl, containing from 10 to 50 carbon atoms are preferably from 25 to 50 carbon atoms.

The term "α-olefin homopolymerization" means the polymerization of monomers so consisting essentially of an α-olefin or a mixture of α-olefins. These waxes preferably have a number-average molecular weight ranging from 400 to 3000 daltons and particularly from 1800 to 2700 daltons. Such polyolefin waxes are described in U.S. Pat. No. 4,060,569 and U.S. Pat. No. 4,239,546. These waxes are especially sold under the names Performa VR 103, Performa VR 253 and Performa VR 260 by the company New Phase Technologies.
(ii) paraffin waxes with a number-average molecular weight of 350 to 600 daltons, for instance the commercial product sold under the name Cerafine 56-58 by the company Baerlocher.
(iii) polymethylene waxes that may be obtained via the Fischer-Tropsch process. They generally have a number-average molecular weight ranging from 350 to 600 daltons. Use will be made in particular of the Cirebelle waxes manufactured by the company Sasol, for instance:
Cirebelle 303: melting point: 51° C.
Cirebelle 305: melting point: 55° C.
Cirebelle 505: melting point: 41° C.

The compositions according to the invention may be prepared according to the standard techniques for anhydrous non-solid compositions, in particular anhydrous creams.

The compositions according to the invention find their application in a large number of treatments, especially cosmetic treatments, for the skin, the lips and the hair, including the scalp, especially for protecting and/or caring for the skin, the lips and/or the hair, and/or for making up skin and/or the lips.

Another subject of the present invention consists of the use of the compositions according to the invention as defined above for the manufacture of products for the cosmetic treatment of the skin, the lips, the nails, the hair, the eyelashes, the eyebrows and/or the scalp, especially care products, antisun products and makeup products.

The cosmetic compositions according to the invention may be used, for example, as makeup products.

The cosmetic compositions according to the invention may be used, for example, as care products and/or antisun products for the face and/or the body, such as balms or more or less thick creams.

A person skilled in the art will choose the said active principle or principles according to the effect desired on the skin, hair, eyelashes, eyebrows or nails.

For caring for and/or making up greasy skin, a person skilled in the art will preferably choose at least one active agent chosen from desquamating agents, sebo-regulating agents or anti-seborrhoeic agents, and astringents.

The composition may also comprise at least one additional ingredient intended to complement the biological effect of these active agents or to afford an immediate visual effect; mention may be made especially of fluorescers, agents for promoting the naturally pinkish coloration of the skin, and abrasive or exfoliant fillers.

To complement and/or optimize the effects imparted by the cosmetic and/or dermatological active agents mentioned above on the keratin materials, it may be advantageous to incorporate into the compositions of the invention other additional ingredients.

In particular, these additional ingredients may impart an immediate visual effect that will be relayed by the biological effect of the active agents mentioned above. They may also, via a mechanical action (e.g.: abrasive fillers), amplify the effect of the biological active agents mentioned above.

Agents for Promoting the Naturally Pinkish Coloration of the Skin

Mention may be made especially of:
- a self-tanning agent, i.e. an agent which, when applied to the skin, especially to the face, can produce a tan effect that is more or less similar in appearance to that which may result from prolonged exposure to the sun (natural tan) or under a UV lamp;
- an additional colouring agent, i.e. any compound that has particular affinity for the skin, which allows it to give the skin a lasting, non-covering coloration (i.e. that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment;

and mixtures thereof.

Examples of self-tanning agents that may especially be mentioned include:
dihydroxyacetone (DHA),
erythrulose, and
the combination of a catalytic system formed from:
manganese and/or zinc salts and oxides, and
alkali metal and/or alkaline-earth metal hydrogen carbonates.

The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazolin-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used.

DHA may be used in free and/or encapsulated form, for example in lipid vesicles such as liposomes, described especially in patent application WO 97/25970.

In general, the self-tanning agent is present in an amount ranging from 0.01% to 20% by weight and preferably in an amount of between 0.1% and 10% of the total so weight of the composition.

Other dyes that allow modification of the colour produced by the self-tanning agent may also be used.

These dyes may be chosen from synthetic or natural direct dyes.

These dyes may be chosen, for example, from red or orange dyes of the fluorane type such as those described in patent application FR 2 840 806. Mention may be made, for example, of the following dyes:
tetrabromofluorescein or eosin known under the CTFA name: CI 45380 or Red 21
phloxin B known under the CTFA name: CI 45410 or Red 27
diiodofluorescein known under the CTFA name: CI 45425 or Orange 10;
dibromofluorescein known under the CTFA name: CI 45370 or Orange 5;
the sodium salt of tetrabromofluorescein known under the CTFA name: CI 45380 (Na salt) or Red 22;
the sodium salt of phloxin B known under the CTFA name: CI 45410 (Na salt) or Red 28;
the sodium salt of diiodofluorescein known under the CTFA name: CI 45425 (Na salt) or Orange 11;
erythrosine known under the CTFA name: CI 45430 or Acid Red 51;
phloxin known under the CTFA name: CI 45405 or Acid Red 98.

These dyes can also be chosen from anthraquinones, caramel, carmine, carbon black, azulene blues, methoxalene, trioxalene, guaiazulene, chamazulene, rose bengal, eosin 10B, cyanosine or daphinine.

These dyes may also be chosen from indole derivatives, for instance the monohydroxyindoles as described in patent FR 2 651 126 (i.e.: 4-, 5-, 6- or 7-hydroxyindole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

Abrasive Fillers or Exfoliants

As exfoliants that may be used in rinse-out compositions according to the invention, examples that may be mentioned include exfoliant or scrubbing particles of mineral, plant or organic origin. Thus, use may be made, for example, of polyethylene beads or powder, nylon powders, polyvinyl chloride powder, pumice, ground materials derived from apricot kernels or walnut shells, sawdust, glass beads, alumina and their mixtures. Mention may also be made of Exfogreen® from Solabia (bamboo extract), extracts of strawberry achenes (strawberry achenes from Greentech), peach kernel powder or apricot kernel powder and, finally, mention may be made, in the field of plant powders with an abrasive effect, of cranberry seed powder.

Mention will be made, as preferred abrasive fillers or exfoliants according to the invention, of peach kernel powder, apricot kernel powder, cranberry seed powder, extracts of strawberry achenes or bamboo extracts.

The examples that follow serve to illustrate the invention without, however, being limiting in nature. In these examples, the amounts of the composition ingredients are given as weight percentages relative to the total weight of the composition.

EXAMPLES

Example 1

Outside the Invention

An example A is performed according to the teaching of patent application WO 02/03935, comprising a non-emulsifying elastomeric organosiloxane, organic screening agents, an oily phase, matting fillers and a humectant, but without the emulsifying silicone surfactant.

| Phase | Ingredients | Ex. 1 (outside the invention) |
|---|---|---|
| A1 | DROMETRIZOLE TRISILOXANE | 3.0 |
| | OCTOCRYLENE | 5.0 |
| | Butylmethoxydibenzoylmethane | 3.0 |
| | Bis(ethylhexyloxyphenol)methoxyphenyltriazine | 3.0 |
| | C12-15 Alkyl benzoate (Tegosoft TN - Evonik Goldschmidt) | 10.0 |
| | Poly C10-30 alkyl acrylate (Intelimer IPA 13-1 - Air Products and Chemicals) | 1.0 |
| A2 | Iron oxides | 0.6 |
| B | Dimethicone and dimethicone crosspolymer (Dow Corning 9041 Silicone Elastomer Blend) | 22.0 |
| | Glycerol | 10.0 |

-continued

| Phase | Ingredients | Ex. 1 (outside the invention) |
|---|---|---|
| | TOCOPHEROL | 0.5 |
| | Dimethicone | 10.9 |
| C | Talc | 15.0 |
| | Silica dimethyl silylate | 2.0 |
| | Polymethylsilsesquioxane (Tospearl 145 A - Momentive Performance Materials) | 2.0 |
| | Titanium dioxide (and) dimethicone (UV-Titan M 195 - Sachtleben) | 12.0 |

The components of B are mixed together in a suitable container (for example a beaker) until a homogeneous mixture is obtained. The mixture is heated to 80° C. The components of phase C are added thereto. The whole is mixed until homogenized. Phase A1 is heated to 80-85° C. in another container, until a homogeneous mixture is obtained. Phase A2 is added with shearing stirring using an Ultra-Turrax type blender. The mixture (A1+A2) is added to the mixture B+C. The whole is mixed until homogenized. The mixture is cooled to 25° C.

It is observed that formula A obtained with the humectant is heterogeneous with the presence of grains and lumps that are unacceptable for cosmetic use.

Example 2

Outside the Invention

A composition 2 outside the invention is prepared under the same conditions as Example 1, comprising a non-emulsifying elastomeric organosiloxane, organic screening agents, an oily phase and matting fillers, without non-silicone thickener.

| Phase | Ingredients | Ex. 2 (outside the invention) |
|---|---|---|
| A1 | DROMETRIZOLE TRISILOXANE | 3.0 |
| | OCTOCRYLENE | 5.0 |
| | Butylmethoxydibenzoylmethane | 3.0 |
| | Bis(ethylhexyloxyphenol)methoxyphenyltriazine | 3.0 |
| | C12-15 Alkyl benzoate (Tegosoft TN - Evonik Goldschmidt) | 10.0 |
| A2 | Iron oxides | 0.6 |
| B | Dimethicone and dimethicone crosspolymer (Dow Corning 9041 Silicone Elastomer Blend) | 33.0 |
| | Dimethicone | 10.9 |
| | TOCOPHEROL | 0.5 |
| C | Silica dimethyl silylate (hydrophobic fumed silica - Aerosil R972 - Evonik Degussa) | 2.00 |
| | Talc | 15.0 |
| | Polymethylsilsesquioxane (Tospearl 145 A - Momentive Performance Materials) | 2.0 |
| | Titanium dioxide (and) dimethicone (UV-Titan M 195 - Sachtleben) | 12.0 |

The components of B are mixed together in a suitable container (for example a beaker) until a homogeneous mixture is obtained. The mixture is heated to 80° C. The components of phase C are added thereto. The whole is mixed until homogenized. Phase A1 is heated to 80-85° C. in another container, until a homogeneous mixture is obtained. Phase A2 is added with shearing stirring using an UltraTurrax-type blender. The mixture (A1+A2) is added to the mixture B+C. The whole is mixed until homogenized. The mixture is cooled to 25° C.

Formula 2 is unstable. Exudation of the oily phase is observed on centrifugation and at 45° C., which is unacceptable for cosmetic use.

Example 3

Anhydrous Antisun Cream

A composition 3 according to the invention is prepared, comprising a non-emulsifying elastomeric organosiloxane, organic screening agents, an oily phase, matting fillers and a non-silicone organic thickener: Poly C10-30 alkyl acrylate (Intelimer IPA 13-1—Air Products and Chemicals) and not containing any humectant.

| Phase | Ingredients | Ex. 3 (invention) |
|---|---|---|
| A1 | DROMETRIZOLE TRISILOXANE | 3.0 |
| | OCTOCRYLENE | 5.0 |
| | Butylmethoxydibenzoylmethane | 3.0 |
| | Bis(ethylhexyloxyphenol)methoxyphenyltriazine | 3.0 |
| | C12-15 Alkyl benzoate (Tegosoft TN - Evonik Goldschmidt) | 10.0 |
| | Poly C10-30 alkyl acrylate (Intelimer IPA 13-1 - Air Products and Chemicals) | 1.0 |
| A2 | Iron oxides | 0.6 |
| B | Dimethicone and dimethicone crosspolymer (Dow Corning 9041 Silicone Elastomer Blend) | 32.0 |
| | Dimethicone | 10.9 |
| | TOCOPHEROL | 0.5 |
| C | Silica dimethyl silylate (hydrophobic fumed silica - Aerosil R972 - Evonik Degussa) | 2.00 |
| | Talc | 15.0 |
| | Polymethylsilsesquioxane (Tospearl 145 A - Momentive Performance Materials) | 2.0 |
| | Titanium dioxide (and) dimethicone (UV-Titan M 195 - Sachtleben) | 12.0 |

The components of B are mixed together in a suitable container (for example a beaker) until a homogeneous mixture is obtained. The mixture is heated to 80° C. The components of phase C are added thereto. The whole is mixed until homogenized. Phase A1 is heated to 80-85° C. in another container, until a homogeneous mixture is obtained. Phase A2 is added with shearing stirring using an UltraTurrax-type blender. The mixture (A1+A2) is added to the mixture B+C. The whole is mixed until homogenized. The mixture is cooled to 25° C.

A homogeneous stable humectant-free formula that contains no grains or lumps and that shows no exudation of oil on centrifugation and at 45° C. is observed after preparation. The composition is easy to apply to the skin without pilling.

Determination of the SPF and of the PPD Index

The following are evaluated:

the in vivo SPF on 15 individuals according to the international method published by Colipa/CTFA SA/JCIA (May 2006):

the UVAPPD PF on 15 individuals according to the recommendations of the JCIA (version of 15/11/1995).

An average SPF of 51.1 and an average UVA index of 21.1 are obtained, i.e. an SPF/PBD ratio of 2.3, thus <3.

Determination of the Matting Effect:

| Zones | Mean level of gloss | | | |
|---|---|---|---|---|
| | T0 | T10 min | T4 h | T6 h |
| Example 3 (invention) | 61.3 ± 9.6 | 49.2 ± 8.5 | 59.7 ± 8.7 | 64.0 ± 9.4 |
| Control | 61.0 ± 10.9 | 62.3 ± 12.7 | 72.0 ± 14.4 | 75.9 ± 16.8 |
| Ex. 3/Control | 0.3 ± 7.6 | −13.0 ± 13.0 | −12.2 ± 10.2 | −11.9 ± 10.2 |

The measurement is performed with the Samba® device, which is composed of a CCD camera and acquisition software. The volunteer is installed on a repositionable table enabling reproducibility of the measurements before and after application of the product. An image of the whole face is acquired using the software, and the analysis is then performed on each half-face. One half-face determined by randomization, receives 300 mg of product, and the other receives nothing. The measurements are taken on the two half-faces at T0, T10 minutes, T4 hours and T6 hours after application of the product.

A statistically significant decrease in the level of gloss measured at T10 min is observed relative to T0, which reflects an immediate matting effect of the product after a single application thereof.

The results of the statistical analysis show that the difference measured at each experimental time on the treated zone is statistically smaller than that measured on the control zone, reflecting a matting effect of the product from 10 minutes and up to 6 hours after a single application.

The invention claimed is:

1. An anhydrous composition in cream form, comprising, in a cosmetically acceptable medium:
   (a) 15-60% by weight of at least one oily phase,
   (b) 2-8% by weight of at least one non-emulsifying elastomeric organopolysiloxane,
   (c) 0.1-40% by weight of a photoprotective system capable of screening out UV radiation,
   (d) 10-40% by weight of least one matting agent, and
   (e) 0.1-10% by weight of at least one non-silicone organic thickener for the oily phase selected from the group consisting of:
   semi-crystalline polymer derived from a monomer bearing a crystallisable chain selected from saturated $C_{14}$ to $C_{22}$ alkyl (meth)acrylate,
   lipophilic polyamide polycondensate, and
   mixtures thereof; wherein the composition does not comprise any humectant.

2. The composition according to claim 1, wherein the non-emulsifying elastomeric organopolysiloxane is selected from the group consisting of those obtained:
   by crosslinking addition reaction of diorganopolysiloxane containing at least one hydrogen bonded to silicon and of a polyoxyalkylene containing at least two ethylenically unsaturated groups;
   by crosslinking addition reaction of a diorganopolysiloxane containing at least one hydrogen bonded to silicon and of polyglycerolated compounds containing ethylenically unsaturated groups, especially in the presence of a platinum catalyst;
   by crosslinking addition reaction of diorganosiloxane containing at least one hydrogen bonded to silicon and of diorganopolysiloxane containing ethylenically unsaturated groups bonded to silicon;
   by dehydrogenation crosslinking condensation reaction between a diorganopolysiloxane containing hydroxyl end groups and a diorganopolysiloxane containing at least one hydrogen bonded to silicon;
   by crosslinking condensation reaction of a diorganopolysiloxane containing hydroxyl end groups and of a hydrolysable organopolysilane;
   by thermal crosslinking of organopolysiloxane; and
   by crosslinking of organopolysiloxane by high-energy radiation.

3. The composition according to claim 1, wherein the non-emulsifying elastomeric organopolysiloxane is obtained via a crosslinking addition reaction (A) of diorganopolysiloxane containing at least two hydrogens each bonded to a silicon, and (B) of diorganopolysiloxane containing at least two ethylenically unsaturated groups bonded to silicon.

4. The composition according to claim 2, wherein the non-emulsifying elastomeric organopolysiloxane is obtained by reaction of dimethylpolysiloxane containing dimethylvinylsiloxy end groups and of methylhydrogenopolysiloxane containing trimethylsiloxy end groups, in the presence of a platinum catalyst.

5. The composition according to claim 1, wherein the non-emulsifying elastomeric organopolysiloxane is in powder form.

6. The composition according to claim 1, wherein the non-emulsifying elastomeric organopolysiloxane is mixed with at least one hydrocarbon-based oil and/or one silicone oil to form a gel.

7. The composition according to claim 6, wherein the oil/non-emulsifying elastomeric organopolysiloxane mixture forming a gel is selected from the group consisting of those having the INCI name:
   Dimethicone and dimethicone/vinyl dimethicone crosspolymer;
   Cyclopentasiloxane and dimethicone/vinyl dimethicone crosspolymer;
   Dimethicone and dimethicone crosspolymer;
   Mineral oil and vinyl dimethicone/lauryl dimethicone crosspolymer;
   Isododecane and vinyl dimethicone/lauryl dimethicone crosspolymer;
   Triethylhexanoin and vinyl dimethicone/lauryl dimethicone crosspolymer; and
   Squalane and vinyl dimethicone/lauryl dimethicone crosspolymer.

8. The composition according to claim 1, wherein the photoprotective system consists of one or more lipophilic or insoluble organic UV-screening agents and/or one or more mineral screening agents.

9. The composition according to claim 8, wherein the lipophilic or insoluble organic UV-screening agents are selected from the group consisting of cinnamic derivatives; anthranilates; salicylic derivatives; dibenzoylmethane derivatives; camphor derivatives; benzophenone derivatives; β,β-diphenylacrylate derivatives; triazine derivatives; benzotriazole derivatives; benzalmalonate derivatives; imidazolines; p-aminobenzoic acid (PABA) derivatives; methylenebis(hydroxyphenylbenzotriazole) derivatives; benzoxazole derivatives; screening polymers and screening silicones; α-alkylstyrene-based dimers; 4,4-diarylbutadienes; merocyanin derivatives; and mixtures thereof.

10. The composition according to claim 9, wherein the lipophilic or insoluble organic UV-screening agents are selected from the group consisting of:
Butylmethoxydibenzoylmethane,
Octocrylene,
Ethylhexyl salicylate,
Bis(ethylhexyloxyphenyl)methoxyphenyltriazine
Diethylhexyl butamido triazone,
Ethylhexyl triazone,
Drometrizole trisiloxane, and mixtures thereof.

11. The composition according to claim 8, wherein the mineral screening agents are coated or uncoated metal oxide pigments.

12. The composition according to claim 1 wherein the matting agent is selected from the group consisting of a rice starch or a corn starch, kaolinite, talc, a pumpkin seed extract, cellulose microbeads, plant fibres, synthetic fibres, expanded acrylic copolymer microspheres, polyamide powders, silica powders, polytetrafluoroethylene powders, silicone resin powders, acrylic polymer powders, wax powders, polyethylene powders, powders of elastomeric crosslinked organopolysiloxane coated with silicone resin, talc/titanium dioxide/alumina/silica composite powders, amorphous mixed silicate powders, silicate particles, and mixtures thereof.

13. The composition according to claim 2, wherein the non-emulsifying elastomeric organopolysiloxane is mixed with at least one hydrocarbon-based oil and/or one silicone oil to form a gel.

14. The composition according to claim 3, wherein the non-emulsifying elastomeric organopolysiloxane is mixed with at least one hydrocarbon-based oil and/or one silicone oil to form a gel.

15. The composition according to claim 4, wherein the non-emulsifying elastomeric organopolysiloxane is mixed with at least one hydrocarbon-based oil and/or one silicone oil to form a gel.

16. The composition according to claim 5, wherein the non-emulsifying elastomeric organopolysiloxane is mixed with at least one hydrocarbon-based oil and/or one silicone oil to form a gel.

17. The composition according to claim 5, wherein the non-emulsifying elastomeric organopolysiloxane is chosen from organopolysiloxanes having the INCI name: Dimethicone/vinyl dimethicone crosspolymer.

* * * * *